United States Patent [19]

Kato et al.

[11] Patent Number: 4,791,127
[45] Date of Patent: Dec. 13, 1988

[54] ALKANESULFONATE DERIVATIVES AND THEIR USE AS INSECTICIDES, ACARICIDES OR NEMATICIDES

[75] Inventors: Shoichi Kato; Shizuo Shimano; Tatsumi Hayaoka, all of Ageo; Akio Masui, Ohmiya, all of Japan

[73] Assignee: Nippon Kayaku Kabushiki Kaisha, Tokyo, Japan

[21] Appl. No.: 913,319

[22] Filed: Sep. 30, 1986

[30] Foreign Application Priority Data

Oct. 7, 1985 [JP] Japan ................................ 60-221846
May 13, 1986 [JP] Japan ................................ 61-107591

[51] Int. Cl.$^4$ ................. C07D 277/34; C07D 277/36; A61K 31/425
[52] U.S. Cl. .................................... 514/369; 548/183; 544/240; 544/309; 544/408; 546/294
[58] Field of Search ................. 548/183; 514/369

[56] References Cited

U.S. PATENT DOCUMENTS

| 3,549,647 | 12/1970 | Johnston | 546/295 |
| 3,829,430 | 8/1974 | Kyriacou | 546/295 |
| 4,500,538 | 2/1985 | Woltersdorf | 514/367 |

FOREIGN PATENT DOCUMENTS

| 142040 | 5/1985 | European Pat. Off. | 544/309 |
| 1079400 | 6/1966 | United Kingdom | 558/56 |
| 1242057 | 4/1968 | United Kingdom | 546/295 |
| 1184876 | 5/1968 | United Kingdom | 514/312 |

OTHER PUBLICATIONS

Chemical Abstracts, vol. 81, 1974, p. 152, Abstract No. 34590e.
Chemical Abstracts, vol. 104, 1986, p. 527, Abstract No. 33858e.

*Primary Examiner*—Alan L. Rotman
*Attorney, Agent, or Firm*—Henry C. Nields

[57] ABSTRACT

Disclosed herein is a compound of the formula:

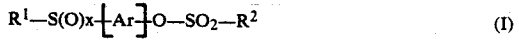

$$R^1-S(O)x-[Ar]-O-SO_2-R^2 \qquad (I)$$

wherein
Ar is pyridine ring, pyridazine ring, pyrimidine ring, pyrazine ring, isoquinoline ring or thiazole ring, and those rings may be substituted by 1~3 of substituents selected from the group consisting of halogen, $C_1$~$C_4$-alkyl, $C_1$~$C_4$-alkoxy, $CF_3$ and nitro,
$R^1$ is $C_1$~$C_8$-alkyl; $C_1$~$C_7$-alkyl which is substituted by 1~3 of F, Cl or Br, $C_1$~$C_4$-alkoxy or $C_1$~$C_4$-alkylthio; $C_3$~$C_7$-cycloalkyl which may be substituted by 1~4 of F, Cl or methyl; $C_3$~$C_6$-cycloalkylmethyl which may be substituted by 1~4 of F, Cl, Br or methyl; allyl, propargyl, phenyl or benzyl; $R^2$ is $C_1$~$C_4$-alkyl which may be substituted by 1~3 of F or Cl,
x is integer of 0, 1 or 2, excepting wherein Ar is pyridine ring which is substituted by $R^1$—S(O)x and —O—$SO_2R^2$ at 2- and 6-position and the $R^1$ is $C_1$~$C_7$-alkyl and the pyridine ring is not further substituted or substituted by 1~3 of halogen.

6 Claims, No Drawings

ALKANESULFONATE DERIVATIVES AND THEIR USE AS INSECTICIDES, ACARICIDES OR NEMATICIDES

DETAILED DESCRIPTION OF THE INVENTION

This invention relates to a compound of the formula:

$$R^1-S(O)_x\text{-}[Ar]\text{-}O-SO_2-R^2 \qquad (I)$$

wherein

Ar is pyridine ring, pyridazine ring, pyrimidine ring, pyrazine ring, isoquinoline ring or thiazole ring and those rings may be substituted by 1-3 of substituents selected from the group consisting of halogen, $C_1$-$C_4$-alkyl, $C_1$-$C_4$-alkoxy, $CF_3$ and nitro, $R^1$ is $C_1$-$C_8$-alkyl; $C_1$-$C_7$-alkyl which is substituted by 1-3 of F, Cl or Br, $C_1$-$C_4$-alkoxy or $C_1$-$C_4$-alkylthio; $C_3$-$C_7$-cycloalkyl which may be substituted by 1-4 of F, Cl or methyl; $C_3$-$C_6$-cycloalkylmethyl which may be substituted by 1-4 of F, Cl, Br or methyl; allyl; propargyl; phenyl or benzyl; $R^2$ is $C_1$-$C_4$-alkyl which may be substituted by 1-3 of F or Cl, x is integer of 0, 1 or 2, excepting wherein Ar is pyridine ring which is substituted by $R^1$—$S(O)_x$ and —O—$SO_2R^2$ at 2- and 6-positions and the $R^1$ is $C_1$-$C_7$-alkyl and the pyridine ring is not further substituted or is substituted by 1-3 of halogen.

The compounds of the present invention can be utilized as an insecticide, acaricide or nematicide in paddy fields, uplands, orchards, forests or the like.

Certain alkanesulfonate derivatives are known to be useful as an active ingredient of an insecticide or a nematicide.

For example, 3-n-butylthiophenyl methanesulfonate and 3-ethylthiophenyl methanesulfonate are described to be useful as an insecticide in Japanese Patent Publication No. 3898/1968 and Japanese Patent Laid-Open No. 98025/1973, respectively. Further, it is reported in J. Agr. Food Chem. 18(1), 57(1970) that 6-chloro-2-pyridyl methanesulfonate has a nematicidal activity.

Alkanesulfonate derivatives of the prior art have an insufficient insecticidal effect on insect pests which have acquired a resistance to organic phosphate or carbamate insecticides or the like, and on insect pests exhibiting a high susceptibility, so that a compound which can prevent such insects with a low dosage has been desired.

The present inventors have found that a compound having a high insecticidal, acaricidal or nematicidal activity can be obtained by substituting the pyridine, pyridazine, pyrimidine, pyrazine, isoquinoline or thiazole rings, with one of alkylthio, alkylsulfinyl or alkylsulfonyl groups as well as with an alkanesulfonyloxy group, as shown by the aforementioned formula (I).

An alkanesulfonate derivative represented by the general formula (I) can be prepared by reacting a compound represented by the general formula:

$$R^1-S(O)_x\text{-}[Ar]\text{-}O-Y^1 \qquad (II)$$

wherein Ar, $R^1$ and x are as defined above and $Y^1$ is a hydrogen, alkali or alkaline earth metal atom, or a compound represented by the general formula:

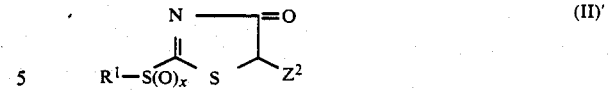

wherein $Z^2$ is hydrogen, halogen, $C_1$-$C_4$-alkyl which may be substituted by halogen, with a sulfonyl halide represented by the general formula:

$$Z^1-SO_2-R^2 \qquad (III)$$

wherein $R^2$ is as defined above, and $Z^1$ is halogen, or a sulfonic acid anhydride represented by the general formula:

$$(R^2SO_2)_2O \qquad (IV)$$

wherein $R^2$ is as defined above, in a solvent, if necessary, in the presence of an acid binding agent, at a temperature of −10° to 100° C., preferably 0° to 40° C., for 0.5 to 10 hours.

Examples of the solvent to be used include water; aromatic hydrocarbons such as benzene, toluene and xylene; aliphatic hydrocarbons such as hexane, heptane and petroleum benzine; halogenated hydrocarbons such as chloroform and dichloromethane; aprotic polar solvents such as dimethylformamide and dimethylsulfoxide; ethers such as diisopropyl ether, diethyl ether, 1,2-dimethoxyethane, tetrahydrofuran and dioxane; nitriles such as acetonitrile and propionitrile; ketones such as acetone, diisopropyl ketone and methyl ethyl ketone. Examples of the acid binding agent of bases include alkali metal hydroxides such as NaOH and KOH; alkaline earth metal hydroxides such as $Ca(OH)_2$ and $Mg(OH)_2$; alkali metal hydrides; alkali metal alcoholates such as sodium alcoholate; alkali metal oxides such as $Na_2O$ and $K_2O$; alkali metal carbonates such as soda ash; sodium amide; aliphatic or aromatic tertiary amines such as triethylamine, dialkyl anilines, pyridines. In addition, silver oxide may be used as an acid binding agent.

Furthermore, a phase transfer catalyst, for example, tetra-n-butylammonium bromide or triethylbenzylammonium chloride, may be also used to obtain the objective alkanesulfonate derivatives in a favorable yield.

Alternatively, a compound represented by the general formula (I) wherein x is 1 or 2 can be prepared as follows:

A compound represented by the general formula:

$$R^1-S\text{-}[Ar]\text{-}O-SO_2-R^2 \qquad (V)$$

wherein Ar, $R^1$ and $R^2$ are as defined above, which corresponds to the general formula (I) wherein x is zero by means of the above-mentioned manner, and then the compound of the formula (V) is treated with an oxidizing agent such as hydrogen peroxide to produce the compound of the formula (I). That is, when the compound represented by the general formula (V) is treated in acetic acid containing 1.0 to 3.0 times by mol as much hydrogen peroxide, preferably at 0° to 60° C. for 3 to 7 hours, a compound represented by the general formula (I) wherein x is 1 can be obtained, while when the compound represented by the general formula (V) is treated in acetic acid containing 2.0 to 5.0 times by mol as much hydrogen peroxide, preferably at 15° to 90° C. for 2 to 24 hours, a compound represented by the general formula (I) wherein x is 2 can be obtained in a high yield. In this treatment, alcohols such as t-butanol, acetone, water or the mixture thereof can be used as a solvent in place of acetic acid.

Examples of the oxidizing agent to be used in oxidizing a compound represented by the general formula (I) wherein x is zero into the corresponding compound of the general formula (I) wherein x is 1 include sodium bromite, organic peroxides, organic halides such as N-bromo-succinimide, bromine, iodine, periodates, nitrogen oxides, ozone, metal oxides, and singlet oxygen as well as hydrogen peroxide. Additionally, this oxidation can be carried out by air or anodic oxidation.

Examples of the oxidizing agents to be used in oxidizing a compound represented by the general formula (I) wherein x is zero or 1 into the corresponding compound represented by the general formula (I) wherein x is 2 include peroxy acid, hydrogen peroxide, halogen, halogenating agents, ozone, oxygen and transition metal catalysts, potassium peroxysulfate, potassium permanganate, dinitrogen tetraoxide, sodium metaperiodate, osmium oxide ($Os^{VIII}$), ruthenium oxide ($Ru^{III}$), sodium dichromate and nitric acid as well as hydrogen peroxide. Additionally, the oxidation with electrode is possible.

The intermediate represented by the general formula (II), for example, wherein Ar is pyridine, can be prepared by the process indicated in U.S. Pat. No. 3,335,146, which can be also applied to the intermediate represented by the general formula (II) wherein Ar is defined as other than pyridine. Further, the other processes shown by the following Course of Reactions are very effective as an alternative synthesis.

Course of Reactions

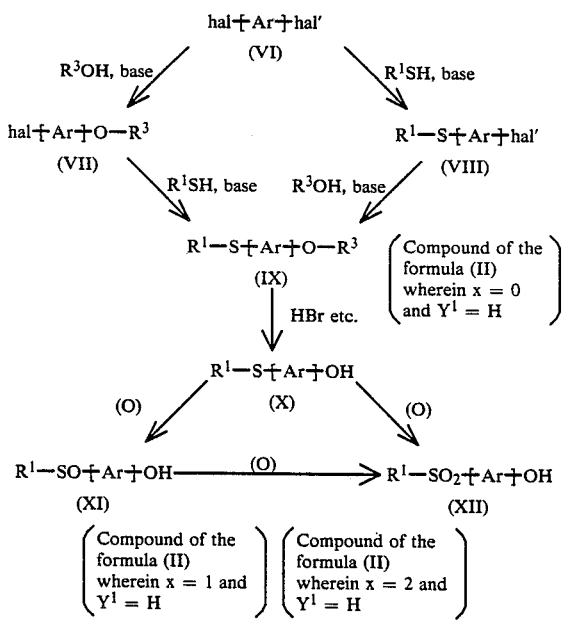

Note:
In the formula, hal and hal' are halogens, same or different from each other; $R^3$ is alkyl, alkenyl, phenyl or phenylalkyl; $R^1$ and Ar are as defined above.

In order to obtain the compound (VII) from (VI), an alcohol represented by the formula $R^3OH$, for example, benzylalcohol is treated by about equivalent mol of sodium hydride in the same solvent as is used in the synthesis of the above-mentioned compound (I) to produce the sodium alcoholate (benzylalcoholate), then to which an equivalent mol of the compound (VI) is added, and agitated at 20° to 100° C., preferably at 50° to 90° C. for 3 to 10 hours to produce the compound (VII) in a high yield. In order to obtain the compound (IX) from the compound (VII), the compound (VII) and an equivalent mol of $R^1SH$ in form of its alkali or alkaline earth metal salt are dissolved in the same solvent as is used in the synthesis of the above-mentioned compound (I), preferably in aprotic polar solvents such as N,N-dimethylacetamide, dimethylformamide and dimethylsulfoxide, and stirred at 20° to 170° C., preferably at 60° to 120° C., for 3 to 10 hours to prepare the compound (IX) in a high yield. Via another route to the compound (IX), the compound (VIII) can be prepared from the compound (VI) in a high yield in a similar manner to the compound (IX) from the compound (VII) aforementioned, and also the compound (IX) from the compound (VIII) is similar to the compound (VII) from the compound (VI). In every process until the above stage, the target compound can be prepared also by utilizing the reaction of double layer system with a phase transfer catalyst in an excellent yield. The compound (X) can be obtained, for example, by treating the compound (IX) with an excess of 47% HBr under stirring at 70° to 100° C. for 3 to 7 hours. In place of HBr, hydrogen iodide (possibly in the presence of red phosphorus), trifluoroacetic acid, concentrated hydrochloric acid, magnesium iodide etherate, aluminium chloride, aluminium bromide, boron tribromide, boron trichloride or boron triiodide may be used. The compound (XI) or (XII) can be prepared from the compound (X), or from the compound (X) or (XI), respectively in a high yield in similar manner to the oxidation process of the compound (V) above.

The intermediate represented by the general formula (II)′, thiazolone derivatives, can be also prepared by a well-known method from rhodanines and alkyl halides. [C. A. 75-35864K: Khim. Geterotsikl. Soedin, 7(2), 189~191 (1971)].

Examples of the pyridine, pyridazine, pyrimidine, pyrazine, isoquinoline and thiazole rings which is Ar in the general formula (I) of the present invention include

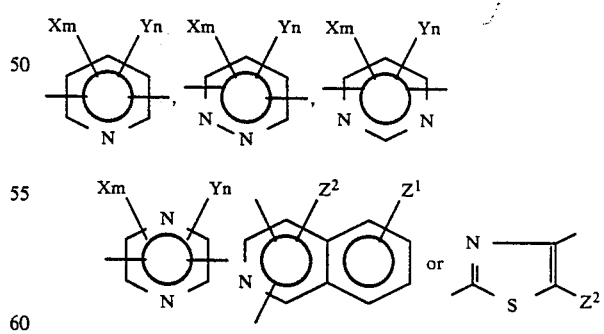

wherein X is a halogen, Y is $C_1$-$C_4$-alkyl, $C_1$-$C_4$-alkoxy, $CF_3$ or nitro, $Z^2$ is hydrogen, halogen, $C_1$-$C_4$-alkyl which may be substituted by halogen, $C_1$-$C_4$-alkoxy, $CF_3$ or nitro, m is 0, 1, 2 or 3 in case of pyridine, or is 0, 1 or 2 in case of pyridazine, pyrimidine or pyrazine, respectively, and n and l are 0, 1 or 2, except that $R^1$—S(O)x— and —O—$SO_2$—$R^2$ are substituted in 2- and 6-positions, $R^1$ is $C_1$–$C_7$-alkyl, m is 0, 1, 2 or 3 and n is zero when Ar is pyridine.

Examples of the halogen include fluorine, iodine, chlorine and bromine; examples of the $C_1$–$C_4$-alkyl include methyl, ethyl, n-propyl, isopropyl and t-butyl; examples of the $C_1$–$C_4$-alkoxy include methoxy, ethoxy, n-propoxy, isopropoxy and n-butoxy. Examples of the $C_1$–$C_8$-alkyl in $R^1$ include methyl, ethyl, n-propyl, isopropyl, n-butyl, isobutyl, s-butyl, t-butyl, n-pentyl, isopentyl, s-pentyl, 2,2-dimethylpropyl, 1,2-dimethylpropyl, n-hexyl, 1,2,2-trimethylpropyl and n-heptyl, and those substituents may be further substituted, for example, by 1 to 3 of fluorine, chlorine or bromine and/or $C_1$–$C_4$-alkoxy and $C_1$–$C_4$-alkylthio, wherein examples of the $C_1$–$C_4$-alkyl include methyl, ethyl, n-propyl, isopropyl, n-butyl, s-butyl and t-butyl, and examples of the $C_3$–$C_7$-cycloalkyl or $C_3$–$C_7$-cycloalkylmethyl include cyclopropyl, cyclopropylmethyl, 2,2-dichlorocyclopropylmethyl, 2,2-dibromocyclopropylmethyl, 2,2-dichloro-1-methyl-cyclopropylmethyl, cyclobutyl, cyclobutylmethyl, 2,2,3,3-tetrafluorobutylmethyl, cyclopentyl, cyclopentylmethyl, cyclohexyl and cyclohexylmethyl. Examples of the $C_1$–$C_4$-alkyl in $R^2$ include methyl, ethyl, n-propyl, isopropyl, n-butyl, isobutyl, s-butyl, t-butyl, chloromethyl, fluoromethyl, trifluoromethyl, bromomethyl, 2-chloroethyl, 3-chloropropyl, 3-bromopropyl and 4-chlorobutyl.

Preferable compounds of the formula (I) in the present invention are those wherein

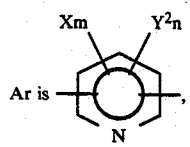

X is halogen, $Y^2$ is $C_1$–$C_4$-alkyl, $C_1$–$C_4$-alkoxy, $CF_3$ or nitro, m and n are 0, 1, 2 or 3 provided that (m+n) is 0–3, $R^1$ is $C_3$–$C_5$-alkyl which may be substituted by F or Cl, $C_3$–$C_6$-cycloalkyl or $C_3$–$C_6$-cycloalkylmethyl, $R^2$ is $CH_3$, $CH_2Cl$ or $C_2H_5$, x is 0, 1 or 2.

Other preferable compounds of the formula (I) in the present invention are those wherein

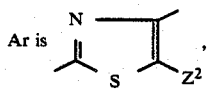

$Z^2$ is hydrogen, halogen, $C_1$–$C_4$-alkyl which may be substituted by halogen,
$R^1$ is $C_2$–$C_5$-alkyl which may be substituted by F or Cl, $C_3$–$C_6$-cycloalkyl or $C_3$–$C_6$-cycloalkylmethyl, allyl, $R^2$ is $CH_3$, $CH_2Cl$ or $C_2H_5$ and x is 0, 1 or 2.

More preferable compounds of the formula (I) in the present invention are those wherein

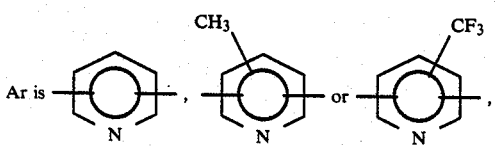

$R^1$ is n—$C_3H_7$, iso—$C_3H_7$, —sec—$C_4H_9$, —n—$C_4H_9$, iso—$C_4H_9$, cyclopentyl or cyclopropylmethyl,
$R^2$ is $CH_3$, $CH_2Cl$ or $C_2H_5$, and x is 0, 1 or 2.

Other more preferable compounds of the formula (I) in the present invention are those wherein

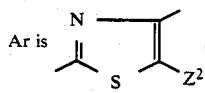

$Z^2$ is hydrogen or bromine, $R^1$ is $C_2H_5$, n—$C_3H_7$, iso—$C_3H_7$, —n—$C_4H_9$, —sec—$C_4H_9$, iso—$C_4H_9$, —$CH_2CH_2CH_2Cl$, —$CH_2CH_2CH_2F$, —$CH_2CH=CH_2$, cyclopentyl or cyclopropylmethyl, $R^2$ is $CH_3$ or $CH_2Cl$ and x is 0, 1 or 2.

The most preferable compound of the formula (I) in the present invention is one selected from the group consisting of the compound of the formula:

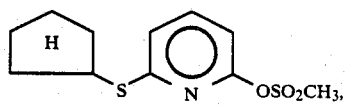

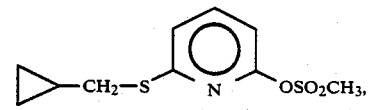

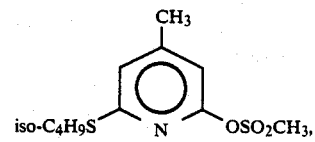

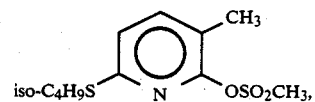

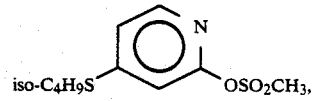

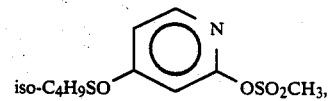

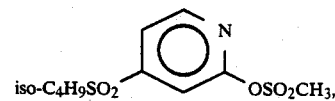

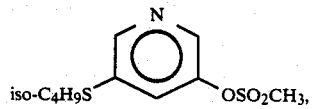

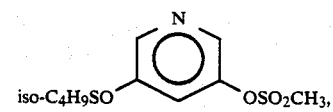

-continued

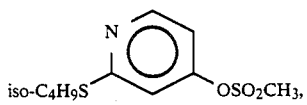

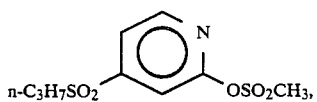

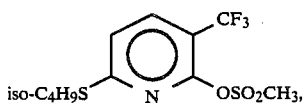

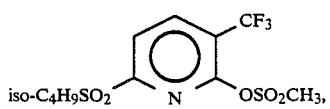

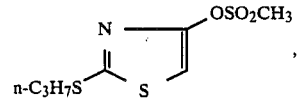

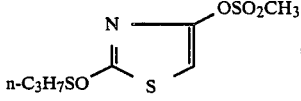

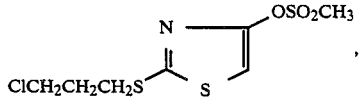

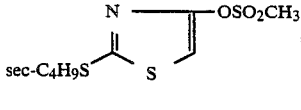

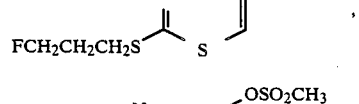

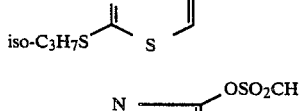

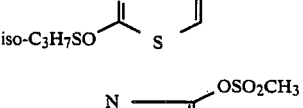

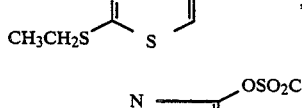

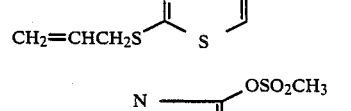

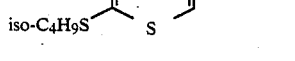

-continued

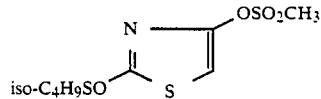

The compounds of the present invention may be used alone according to the purpose of application in their practical use, but they are generally formulated by blending suitable adjuvants to improve or stabilize the effects thereof and used as such or after diluted if necessary. The compounds of the invention can be formulated in the conventional manners well-known in the art in any convenient form such as dust, granule, microgranule, wettable powder, flowable powder, emulsion, microcapsule, oil, aerosol, heating fumigant (e.g. mosquito repellent of an incense type or electric type), fuming agents such as fogging, non-heating fumigant, or toxic feed.

Examples of said adjuvants are carried (i.e. diluent) and other adjuvants such as spreader, emulsifying agent, wetting agent, dispersing agent, fixing agent or disintegrator. Examples of the liquid carrier are aromatic hydrocarbons such as toluene or xylene; alcohols such as methanol, butanol or glycol; ketones such as acetone; amides such as dimethylformamide; sulfoxides such as dimethyl sulfoxide; methylnaphthalene; cyclohexane; animal or vegetable oils; fatty acids and esters thereof or the like as well as petroleum fractions such as keronsine or gas oil.

Examples of the solid carrier are clay, kaolin, talc, diatomaceous earth, silica, calcium carbonate, montmorillonite, bentonite, feldspar, quartz, alumina or saw dust.

Surfactants are generally used as an emulsifying or dispersing agent. Examples of them are anionic, cationic, non-ionic and ampholytic surfactants such as sodium salt of higher alcohol sulfate, stearyltrimethylammonium chloride, polyoxyethylene alkylphenyl ether or laurylbetaine.

Examples of the spreaders are polyoxyethylene nonylphenyl ether and polyoxyethylene lauryl ether. Examples of the wetting agents are polyoxyethylene nonylphenyl ether and dialkyl sulfosuccinates. Examples of the fixing agents are carboxymethylcellulose and polyvinyl alcohol. Examples of the disintegrators are sodium lignin-sulfonate and sodium laurylsulfate.

Furthermore, it is possible to blend two or more compounds of the present invention to obtain improved insecticidal and acaricidal activities. In addition, it is also possible to use a compound of the present invention simultaneously with other physiologically active substances such as pyrethroids, e.g., allethrin, phthalthrin, permethrin, decamethrin, fenvalerate, or $\alpha$-cyano-3-phenoxybenzyl 2,2-dichloro-1-(4-ethoxyphenyl)cyclopropane-1-carboxylate and various isomers thereof, pyrethrum extract; organophosphorus pesticides, e.g., DDVP, fenitrothion, diazinon or temefos; carbamate pesticides, e.g., NAC, MTMC, BPMC or pirimor; other pesticides, acaricides or fungicides, nematicides, herbicides, plant growth regulators, fertilizers, BT, insect hormones or other pesticides, thereby affording a multipurpose composition which exhibits an improved effect and further a synergistic effect, if things go well.

It is further possible to increase the effect of the composition several times as much by adding synergists for pyrethroids such as piperonyl butoxide, sulfoxide or safroxane.

Although the compounds of the present invention are stable to light, heat, and oxidation or the like, antioxidant or ultraviolet absorbers such as phenols, e.g., BHT or BHA; arylamines, e.g., α-naphthyl amine; or benzophenone compound may be added as a stabilizer to prepare a composition which exhibits a higher stability, if necessary.

The content of active ingredients in the composition of the present invention varies depending on the conditions of use such as formulation form or application method, and is usually from 0.2 to 95% by weight, preferably from 0.5 to 80% by weight, although the active ingredients may be used alone in a special case.

The composition of the present invention may be used in an amount which depends on the conditions such as formulation form, method or season for application. It is usually used in an amount of 10 to 300 g/10a (a=100 m$^2$), preferably 15 to 200 g/10a in terms of the active ingredient for the agricultural and horticultural pesticide and the insecticide for forestry and pasturage, and in an amount of 2 to 200 mg/m$^2$, preferably 5 to 100 mg/m$^2$ in terms of the active ingredient for the hygienic insecticide. For example, 15 to 120 g/10a of the active ingredient is used in the case of dust, 30 to 240 g/10a thereof is used in the case of granule, and 40 to 250 g/10a thereof is used in the case of emulsion. However, it may be possible, or even necessary, to use the active ingredient in an amount which is outside the range as specified above, in a special case.

The insect pests on which the insecticides, acaricides and nematicides of the present invention are effective are as follows: Hemiptera such as *Nephotettix cincticeps, Sogatella furcifera, Niraparvata lugens, Laodelphax striatellus, Riptortus clavatus, Nezara viridula, Stephanis nashi, Trialeurodes vaporaviorum, Aphis gossypii, Myzus persicae* and *Vnaspis yanonensis;* Lepidoptera such as *Phyllonorycter ringoneella, Plutella xylostella, Promalactis inonisema, Adoxophyes orana, Leguminivora glycinivorella, Cnaphalocrocis medinalis, Chilo suppressalis, Ostrinia furnacalis, Mamestra brassicae, Pseudaletia separata, Spodoptera litura, Parnara guttata* and *Pieris rapae crucivora;* Coleoptera such as *Anomala cuprea, Popillia japonica, Echinocnemus soqameus, Lissorhoptrus oryzophilus, Anthonomus grandis, Oulema oryzae, Diabrotica undecimpunctata, Leptinotarsa decemlineata, Anthrenus verbasci, Tenebroides mauritanicus, Sitophilus zeamais, Henosepilachna vigintioctopunctata, Callosobruchus chinensis, Monochamus alternatus* and *Aulacophora femovalis;* Hymenoptera such as *Athalia rosae japonensis* and *Arge similis;* Diptera such as *Culex pipiens fatigans, Aedes aegypti,* Asphondylia sp., *Hylemya platura, Musca domestica vicina, Dacus cucurbitae* and *Agromyza oryzae;* Aphaniptera such as *Pulex irritans, Xenopsylla cheopis* and *Ctenocephalides canis;* Thysanoptera such as *Scirtothrips dorsalis, Thrips tabaci, Thrips palmi* and *Baliothrips biformis;* Anoplura such as *Pediculus humanus corporis* and *Pthirus pubis;* Psocoptera such as *Trogium pulsatorium* and *Liposcelis bostrychophus;* Orthoptera such as *Gryllotalpa africana, Locusta migratoria, Oxya yezoensis, Blattella germanica* and *Periplaneta fuliginosa;* and Acarina such as *Tetranychus urticae, Panonychus citri, Tetranychus cinnabarinus, Tetranychus kanzawai* and *Rhizoglyphus echinopus.*

The nematodes on which the nematicides of the present invention are effective are Tylenchida such as *Heterodera glycines, Heterodera elachist, Meloidogyne incognita, Pratylenchus neglectus, Aphelenchoides besseyi, Aphelenchoides ritzemabosi* and *Bursa phelenchus lignicolus.*

The compounds of the present invention can prevent insect pests effectively by contacting them, or control insect pests on leaves by applying the compounds at the root of plants. Thus, the compound is an excellent insecticide, acaricide or nematicide which has characteristics as a systemic insecticide with scarce phytotoxicity on the host crops.

Now, the present invention will be described by Examples.

SYNTHESIS EXAMPLE:

Synthesis Example 1: Synthesis of 6-isobutylthio-2-pyrazyl methanesulfonate (Compound No. 14):

(1) Synthesis of 2-benzyloxy-6-chloropyrazine as an intermediate:

7.6 g of benzylalcohol was dissolved in 65 ml of benzene, and 2.8 g of 60% sodium hydride was added little by little to the solution under stirring not so as to foam too much at room temperature. After the addition, stirring was continued for 10 min. at room temperature, followed by reflux for 1 hour. Subsequently, the solution was cooled to 50° to 60° C., and added dropwise with a solution of 10 g of 2,6-dichloropyrazine in 65 ml of benzene for 10 min. Then, after reflux for 4 hours, the reaction was finished. After cooling below 10° C., about 100 ml of water was added, and the separated benzene layer was collected. The residue obtained by distilling off the solvent was purified by silica-gel column chromatography (developing solvent: n-hexane and ethyl acetate) to obtain 12.8 g of 2-benzyloxy-6-chloropyrazine as a colourless oil (yield: 86.5%)

$n_D^{25}$ 1.5818.

(2) Synthesis of 2-benzyloxy-6-isobutylthiopyrazine as an intermediate:

12.8 g of 2-benzyloxy-6-chloropyrazine obtained by the process described in (1) and 11.2 g of potassium salt of isobutylmercaptane were dissolved in 50 ml of N,N-dimethylacetamide, followed by stirring at 70° to 80° C. for 7 hours. After cooling the reaction mixture was poured into 500 ml of water and extracted twice by 150 ml of toluene to obtain an organic layer, which was further washed with water and then with saturated aqueous solution of common salt, followed by distilling off the solvent. The obtained residue was purified by silica-gel column chromatography (developing solvent: toluene and n-hexane) to obtain 11.1 g of 2-benzyloxy-6-isobutylthiopyrazine as a pale yellow oil (yield: 69.7%).

$n_D^{25}$ 1.5790

PMR(CDCl$_3$)δ: 1.02[6H, d, —SCH$_2$CH(CH$_3$)$_2$], 1.94 [1H, m, —SCH$_2$CH(CH$_3$)$_2$], 3.02[2H, d, —SCH$_2$CH(CH$_3$)$_2$], 5.40 [2H, s, —OCH$_2$Ph], 7.39 [5H, s, proton in benzene ring], 7.90 [1H, s, proton in pyrazine ring], 8.03 [1H, s, proton in pyrazine ring] ppm.

(3) Synthesis of 2-hydroxy-6-isobutylthiopyrazine as an intermediate:

7.0 g of 2-benzyloxy-6-isobutylthiopyrazine obtained by the process described in (2) and 50 ml of acetic acid were mixed and added with 13.2 ml of 47% hydrobromic acid under stirring. The reaction was finished by stirring at 80° to 90° C. for 4 hours. The reaction mixture was cooled to room temperature and then poured into about 300 ml of chilled water. The pH of the solution was adjusted by 20% aqueous caustic soda and extracted thrice by ether. The ether layer was washed with water and then with saturated aqueous solution of common salt, followed by drying with anhydrous sodium sulfate. To the residue obtained after distilling off the solvent a small amount of the solvent mixture of toluene was added and n-hexane (1:1), was added and the mixture was filtrated to separate 4.0 g of the objective 2-hydroxy-6-isobutylpyrazine as a pale brown crystal (yield: 85.1%).

m.p. 130° to 131° C.

PMR(CDCl$_3$) δ: 1.05 [6H, d, —SCH$_2$CH(CH$_3$)$_2$], 1.93 [1H, m, —SCH$_2$CH(CH$_3$)$_2$], 2.97 [2H, d, —SC$\underline{H}_2$CH(CH$_3$)$_2$], 7.57 [1H, s, proton in pyrazine ring], 8.00 [1H, s, proton in pyrazine ring], 15.50 [1H, bs,

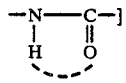

] ppm.

(4) Synthesis of 6-isobutylthio-2-pyrazyl methanesulfonate (Compound No. 14) as an objective compound:

4.0 g of 2-hydroxy-6-isobutylthiopyrazine obtained by the process described in (3) and 2.4 ml of methanesulfonyl chloride were dissolved in 20 ml of N,N-dimethylacetamide and cooled to 0° to 10° C. 5.3 ml of triethylamine was added dropwise to the solution under stirring for 10 min, and then the temperature of the solution was raised gradually to room temperature, followed by stirring for 5 hours to accomplish the reaction. The reaction mixture was poured into 200 ml of water and extracted twice by ethyl acetate. The organic layer was washed with water and distilled to remove the solvent. The obtained residue was purified by silica-gel column chromatography (developer: toluene and n-hexane) to obtain 4.1 g of the objective 6-isobutylthio-2-pyrazyl methanesulfonate as a pale brown crystal (yield: 72.0%).

m.p 65° to 66° C.

PMR(CDCl$_3$) δ: 1.05 [6H, d, —SCH$_2$CH(CH$_3$)$_2$], 1.98 [1H, m, —SCH$_2$C$\underline{H}$(CH$_3$)$_2$], 3.03 [2H, d, —SC$\underline{H}_2$CH(CH$_3$)$_2$], 3.46 [3H, s, —OSO$_2$C$\underline{H}_3$], 8.08 [1H, s, proton in pyrazine ring], 8.40 [1H, s, proton in pyrazine ring] ppm.

Synthesis Example 2: Synthesis of 6-isobutylsulfinyl-2-pyrazyl methanesulfonate (Compound No. 15):

1.2 g of 6-isobutylthio-2-pyrazyl methanesulfonate (Compound No. 14) obtained by the process described in Synthesis Example 1 was dissolved in 10 ml of acetic acid. 1.2 ml of 30% aqueous hydrogen peroxide was added under stirring at room temperature during 30 min. After that, stirring was continued at room temperature for 3 hours and at 50° C. for further 3 hours to accomplish the reaction. The reaction mixture was cooled below room temperature and poured into 150 ml of chilled water. The organic layer obtained by extracting by methylene chloride three times was washed with water and 5% aqueous caustic soda twice, and then with water and saturated aqueous solution of common salt. The residue obtained by distilling off the solvent was purified by silica-gel column chromatography (developer: ethylacetate and n-hexane) to obtain 1.0 g of the objective 6-isobutylsulfinyl-2-pyrazyl methanesulfonate as a pale yellow oil (yield: 79.7%).

n$_D^{25}$ 1.5308

PMR(CDCl$_3$) δ: 1.11, 1.21 [6H, d, d, —SOCH$_2$CH(CH$_3$)$_2$], 2.36, 2.43 [1H, m, m, —SOCH$_2$C$\underline{H}$(CH$_3$)], 2.92, 2.95 [2H, d, d, —SOC$\underline{H}_2$CH(CH$_3$)$_2$], 3.51 [3H, s, —OSO$_2$CH$_3$], 8.63 [1H, s, proton in pyrazine ring], 9.15 [1H, s, proton in pyrazine ring] ppm.

Synthesis Example 3: Synthesis of 4-isobutylthio-2-pyridyl methanesulfonate (Compound No. 30):

1.3 g of 4-isobutylthio-2-pyridone (m.p. 119° to 120° C.) and 0.7 ml of methanesulfonyl chloride were dissolved in 10 ml of methylene chloride, and cooled below 10° C. 1.5 ml of triethylamine was added dropwise to the solution with stirring. By stirring at room temperature for 4 hours, the reaction was completed. The reaction solution was poured into 100 ml of water, followed by addition of 100 ml of methylene chloride for separation. The methylene chloride layer was washed with water and saturated aqueous solution of common salt, then distilled to remove the solvent. The obtained residue was purified by silica-gel column chromatography (developer: benzene and n-hexane) to obtain 1.7 g of the objective 4-isobutylthio-2-pyridyl methanesulfonate (yield: 91.6%) as a colourless oil, which were allowed to stand to crystallization.

m.p 34° to 35° C.

PMR(CDCl$_3$) δ: 1.06 [6H, d, —SCH$_2$CH(CH$_3$)$_2$], 1.97 [1H, m, —SCH$_2$C$\underline{H}$(CH$_3$)$_2$], 2.86 [2H, d, —SC$\underline{H}_2$CH(CH$_3$)$_2$], 3.49 [3H, s, —OSO$_2$C$\underline{H}_3$], 6.88 [1H, d, proton in pyridine ring], 7.06 [1H, d-d, proton in pyridine ring], 8.08 [1H, d, proton in pyridine ring] ppm.

Synthesis Example 4: Synthesis of 4-isobutylsulfonyl-2-pyridyl methanesulfonate (Compound No. 32):

1.7 g of 4-isobutylthio-2-pyridyl methanesulfonate (Compound No. 30) obtained by the process described in Synthesis Example 3 was dissolved in 10 ml of acetic acid, followed by adding 1.5 ml of 30% aqueous hydrogen peroxide below 10° C. and stirring at room temperature for 2 hours. Further, 0.5 ml of 30% aqueous hydrogen peroxide was added to the reaction mixture, which was stirred at 40° C. for 8 hours to accomplish the reaction. After cooling, the reaction solution was poured into 100 ml of chilled water and extracted three times with 100 ml of methylene chloride. The organic layer was washed twice with 5% aqueous caustic soda, then with water and saturated aqueous solution of common salt, followed by distilling off the solvent. The obtained residue was purified by silica-gel column chromatography (developer: ethyl acetate and n-hexane) to obtain 1.3 g of the objective 4-isobutylsulfonyl-2-pyridyl methanesulfonate as a colourless crystal (yield: 68.2%).

m.p. 75.5° to 76.5° C.

PMR(CDCl$_3$) δ: 1.10 [6H, d, —SCH$_2$CH(CH$_3$)$_2$], 2.29 [1H, m, —SCH$_2$C$\underline{H}$(CH$_3$)$_2$], 3.06 [2H, d, —SC$\underline{H}_2$CH(CH$_3$)$_2$], 3.55 [3H, s, —OSO$_2$C$\underline{H}_3$], 7.59 [1H, d, proton in pyridine ring], 7.76 [1H, d-d, proton in pyridine ring], 8.65 [1H, d, proton in pyridine ring] ppm.

Synthesis Example 5: Synthesis of 5-isobutylthio-3-pyridyl trifluoromethylsulfonate (Compound No. 45):

A mixture of 0.5 g of 5-isobutylthio-3-pyridinol (m.p. 83° to 84° C.) and 0.5 ml of pyridine was cooled to 5° to 10° C. 1 g of trifluoromethanesulfonic anhydride was added with stirring to the mixture, which was stirred at this temperature for 30 min. The reaction was continued at room temperature for further 5 hours. The reaction solution was poured into 100 ml of chilled water and extracted twice by 50 ml of toluene. The toluene layer obtained was washed twice by water. The residue obtained by distilling off the solvent was purified by silica-gel column chromatography (developer: ethylacetate and n-hexane) to obtain 0.9 g of the objective 5-isobutylthio-3-pyridyl trifluoromethanesulfonate as a colourless oil (yield: 95.1%).

$n_D^{25}$ 1.4875

PMR(CDCl$_3$) δ: 1.07 [6H, d, —SCH$_2$CH(CH$_3$)$_2$], 1.91 [1H, m, —SCH$_2$CH(CH$_3$)$_2$], 2.87 [2H, d, —SCH$_2$CH(CH$_3$)$_2$], 7.49 [1H, t, proton in pyridine ring], 8.33 [1H, d, proton in pyridine ring], 8.53 [1H, d, proton in pyridine ring] ppm.

Other compounds of the present invention were synthesized according to the same procedure as the ones described in Synthesis Examples 1 to 5. Typical compounds among the obtained ones shown in Table 1.

TABLE 1

$$R^1-S(O)_x \!\!\leftarrow\!\! Ar \!\!\rightarrow\!\! O-SO_2-R^2 \quad (I)$$

| Compound No. | formula | m.p. or b.p. (refractive index) | appearance |
|---|---|---|---|
| 1 | (cyclohexyl)-S-(pyridine)-OSO$_2$CH$_3$ | ($n_D^{25}$ 1.5620) | colourless oil |
| 2 | (cyclohexyl)-SO$_2$-(pyridine)-OSO$_2$CH$_3$ | ($n_D^{25}$ 1.5370) | colourless oil |
| 3 | (cyclopropyl-CH$_2$)-S-(pyridine)-OSO$_2$CH$_3$ | ($n_D^{25}$ 1.5635) | pale yellow oil |
| 4 | (cyclopropyl-CH$_2$)-S-(pyridine)-OSO$_2$CH$_2$CH$_3$ | ($n_D^{25}$ 1.5569) | pale yellow oil |
| 5 | (phenyl-CH$_2$)-S-(pyridine)-OSO$_2$CH$_3$ | mp 71–72° C. | colourless crystal |
| 6 | (phenyl-CH$_2$)-SO$_2$-(pyridine)-OSO$_2$CH$_3$ | mp 116–117° C. | colourless crystal |
| 7 | (CH$_3$)$_2$CHCH$_2$S-(pyridine)-OSO$_2$CH$_3$ | mp 61–63° C. | colourless crystal |
| 8 | (CH$_3$)$_2$CHCH$_2$S-(4-CH$_3$-pyridine)-OSO$_2$CH$_3$ | ($n_D^{25}$ 1.5242) | colourless oil |

TABLE 1-continued $$R^1-S(O)_x+Ar+O-SO_2-R^2 \quad (I)$$

| Compound No. | formula | m.p. or b.p. (refractive index) | appearance |
|---|---|---|---|
| 9 | CH₃CH₂CH₂S—[pyrimidine(4-CH₃)]—OSO₂CH₃ | ($n_D^{25}$ 1.5365) | colourless oil |
| 10 | (CH₃)₂CHCH₂S—[pyrimidine]—OSO₂CH₃ | ($n_D^{25}$ 1.5409) | colourless oil |
| 11 | (CH₃)₂CHCH₂S—[pyridine(3-CH₃)]—OSO₂CH₃ | ($n_D^{25}$ 1.5331) | colourless oil |
| 12 | CH₃S—[pyrimidine(4-CH₃)]—OSO₂CH₃ | bp 146–154° C./ 0.6–0.65 mmHg | colourless oil |
| 13 | (CH₃)₂CHCH₂S—[pyridazine]—OSO₂CH₃ | mp 86–87° C. | pale yellow crystal |
| 14 | (CH₃)₂CHCH₂S—[pyridine]—OSO₂CH₃ | mp 65–66° C. | brown crystal |
| 15 | (CH₃)₂CHCH₂SO—[pyridine]—OSO₂CH₃ | ($n_D^{25}$ 1.5308) | pale yellow oil |
| 16 | (CH₃)₂CHCH₂SO₂—[pyridine]—OSO₂CH₃ | ($n_D^{25}$ 1.5183) | pale yellow oil |
| 17 | (CH₃)₂CHCH₂S—[isoquinoline]—OSO₂CH₃ | mp 98–99° C. | pale yellow crystal |

TABLE 1-continued $$R^1-S(O)x+Ar+O-SO_2-R^2 \quad (I)$$

| Compound No. | formula | m.p. or b.p. (refractive index) | appearance |
|---|---|---|---|
| 18 | (CH₃)₂CHCH₂SO-[isoquinoline]-OSO₂CH₃ | mp 120–121° C. | colourless crystal |
| 19 | (CH₃)₂CHCH₂SO₂-[isoquinoline]-OSO₂CH₃ | mp 64–66° C. | colourless crystal |
| 20 | (CH₃)₂CHCH₂S-[isoquinoline]-OSO₂CH₃ | mp 100–101° C. | colourless crystal |
| 21 | (CH₃)₂CHCH₂SO-[isoquinoline]-OSO₂CH₃ | mp 106–107° C. | colourless crystal |
| 22 | (CH₃)₂CHCH₂SO₂-[isoquinoline]-OSO₂CH₃ | mp 116–117° C. | pale yellow crystal |
| 23 | (CH₃)₂CHCH₂S-[4-methylpyridine]-OSO₂CH₃ | mp 56.5–57.5° C. | colourless crystal |
| 24 | (CH₃)₂CHCH₂SO-[4-methylpyridine]-OSO₂CH₃ | ($n_D^{25}$ 1.5285) | colourless oil |

TABLE 1-continued $$R^1-S(O)x+Ar+O-SO_2-R^2 \qquad (I)$$

| Compound No. | formula | m.p. or b.p. (refractive index) | appearance |
|---|---|---|---|
| 25 | 4-CH₃, 2-(i-C₃H₇CH₂SO₂), 6-(OSO₂CH₃)-pyridine [(CH₃)₂CHCH₂SO₂– and –OSO₂CH₃ on 4-methylpyridine] | mp 79.5–80° C. | colourless crystal |
| 26 | 3-NO₂, 2-(i-C₃H₇CH₂S), 6-(OSO₂CH₃)-pyridine | mp 88–89° C. | yellow crystal |
| 27 | 3-NO₂, 2-(i-C₃H₇CH₂SO), 6-(OSO₂CH₃)-pyridine | mp 99–100° C. | yellow crystal |
| 28 | 3-NO₂, 2-(i-C₃H₇CH₂SO₂), 6-(OSO₂CH₃)-pyridine | mp 114–115° C. | pale yellow crystal |
| 29 | 3-CH₃, 6-(i-C₃H₇CH₂S), 2-(OSO₂CH₃)-pyridine | mp 46–47° C. | colourless crystal |
| 30 | 4-(i-C₃H₇CH₂S), 2-(OSO₂CH₃)-pyridine | mp 34–35° C. | colourless crystal |
| 31 | 4-(i-C₃H₇CH₂SO), 2-(OSO₂CH₃)-pyridine | mp 79–80° C. | colourless crystal |
| 32 | 4-(i-C₃H₇CH₂SO₂), 2-(OSO₂CH₃)-pyridine | mp 75.5–76.5° C. | colourless crystal |
| 33 | 4-(i-C₃H₇CH₂S), 2-(OSO₂CH₂CH₃)-pyridine | ($n_D^{25}$ 1.5371) | pale yellow oil |

TABLE 1-continued $$R^1-S(O)_x-Ar-O-SO_2-R^2 \quad (I)$$

| Compound No. | formula | m.p. or b.p. (refractive index) | appearance |
|---|---|---|---|
| 34 | (CH₃)₂CHCH₂S-pyridine-OSO₂CH₃ (2,4-substituted) | ($n_D^{25}$ 1.5440) | pale yellow oil |
| 35 | (CH₃)₂CHCH₂SO₂-pyridine-OSO₂CH₃ (2,4-substituted) | ($n_D^{25}$ 1.5229) | pale yellow oil |
| 36 | (CH₃)₂CHCH₂S-pyridine-OSO₂CH₃ (3,5-substituted) | ($n_D^{25}$ 1.5470) | yellow oil |
| 37 | (CH₃)₂CHCH₂SO-pyridine-OSO₂CH₃ (3,5-substituted) | mp 87–88° C. | colourless crystal |
| 38 | pyridine-2-SCH₂CH(CH₃)₂, 3-OSO₂CH₃ | ($n_D^{25}$ 1.5434) | colourless oil |
| 39 | pyridine-2-SOCH₂CH(CH₃)₂, 3-OSO₂CH₃ | mp 65–67° C. | colourless crystal |
| 40 | pyridine-2-SO₂CH₂CH(CH₃)₂, 3-OSO₂CH₃ | mp 67–68° C. | colourless crystal |
| 41 | (CH₃)₂CHCH₂S-pyridine-OSO₂CH₃ | ($n_D^{25}$ 1.5390) | pale yellow oil |
| 42 | (CH₃)₂CHCH₂SO-pyridine-OSO₂CH₃ | mp 96–97° C. | colourless crystal |
| 43 | (CH₃)₂CHCH₂SO₂-pyridine-OSO₂CH₃ | mp 110–111° C. | colourless crystal |

TABLE 1-continued $$R^1-S(O)_x-(Ar)-O-SO_2-R^2 \quad (I)$$

| Compound No. | formula | m.p. or b.p. (refractive index) | appearance |
|---|---|---|---|
| 44 | (CH₃)₂CHS-[pyridine]-OSO₂CH₃ | mp 38–40° C. | colourless crystal |
| 45 | (CH₃)₂CHCH₂S-[pyridine]-OSO₂CF₃ | ($n_D^{25}$ 1.4875) | colourless oil |
| 46 | CH₃CH₂CH₂S-[pyridine]-OSO₂CH₃ | ($n_D^{25}$ 1.5511) | colourless oil |
| 47 | CH₃CH₂CH₂SO-[pyridine]-OSO₂CH₃ | ($n_D^{25}$ 1.5434) | colourless oil |
| 48 | CH₃CH₂CH₂SO₂-[pyridine]-OSO₂CH₃ | mp 56–57° C. | colourless crystal |
| 49 | cyclohexyl-S-[pyridine]-OSO₂CH₃ | mp 79–80° C. | colourless crystal |
| 50 | cyclohexyl-SO-[pyridine]-OSO₂CH₃ | mp 86.5–87° C. | colourless crystal |
| 51 | cyclohexyl-SO₂-[pyridine]-OSO₂CH₃ | mp 74–75° C. | colourless crystal |
| 52 | Cl₂(CH₃)cyclopropyl-CH₂S-[pyridine]-OSO₂CH₃ | | |
| 53 | Cl₂(CH₃)cyclopropyl-CH₂SO-[pyridine]-OSO₂CH₃ | | |
| 54 | Cl₂(CH₃)cyclopropyl-CH₂SO₂-[pyridine]-OSO₂CH₃ | | |

TABLE 1-continued $$R^1-S(O)x-Ar-O-SO_2-R^2 \quad (I)$$

| Compound No. | formula | m.p. or b.p. (refractive index) | appearance |
|---|---|---|---|
| 55 | CH₃CH₂CH₂S—[pyridine with N, OCH₃, OSO₂CH₃] | | |
| 56 | CH₃CH₂CH₂SO—[pyridine with N, OCH₃, OSO₂CH₃] | | |
| 57 | CH₃CH₂CH₂SO₂—[pyridine with N, OCH₃, OSO₂CH₃] | | |
| 58 | CH₂=CHCH₂S—[pyridine with N, OSO₂CH₃] | | |
| 59 | CH₂=CHCH₂SO—[pyridine with N, OSO₂CH₃] | | |
| 60 | CH₂=CHCH₂SO₂—[pyridine with N, OSO₂CH₃] | | |
| 61 | FCH₂CH₂CH₂S—[pyridine with N, OSO₂CH₃] | | |
| 62 | FCH₂CH₂CH₂SO—[pyridine with N, OSO₂CH₃] | | |
| 63 | FCH₂CH₂CH₂SO₂—[pyridine with N, OSO₂CH₃] | | |
| 64 | CF₃CH₂S—[pyridine with N, OSO₂CH₃] | | |
| 65 | CF₃CH₂SO—[pyridine with N, OSO₂CH₃] | | |
| 66 | CF₃CH₂SO₂—[pyridine with N, OSO₂CH₃] | | |

TABLE 1-continued $$R^1-S(O)x+Ar+O-SO_2-R^2 \quad (I)$$

| Compound No. | formula | m.p. or b.p. (refractive index) | appearance |
|---|---|---|---|
| 67 | 3-($CH_3CH_2CH_2S$)-5-($OSO_2CH_3$)-pyridine | | |
| 68 | 3-($CH_3CH_2CH_2SO$)-5-($OSO_2CH_3$)-pyridine | | |
| 69 | 3-($CH_3CH_2CH_2SO_2$)-5-($OSO_2CH_3$)-pyridine | | |
| 70 | 2-(cyclobutyl-$CH_2S$)-6-($OSO_2CH_3$)-pyridine | | |
| 71 | 2-(cyclobutyl-$CH_2SO$)-6-($OSO_2CH_3$)-pyridine | | |
| 72 | 2-(cyclobutyl-$CH_2SO_2$)-6-($OSO_2CH_3$)-pyridine | | |
| 73 | 2-(cyclohexyl-$CH_2S$)-6-($OSH_2CH_3$)-pyridine | | |
| 74 | 2-(cyclohexyl-$CH_2SO$)-6-($OSO_2CH_3$)-pyridine | | |
| 75 | 2-(cyclohexyl-$CH_2SO_2$)-6-($OSO_2CH_3$)-pyridine | | |
| 76 | 2-($ClCH_2CH_2CH_2S$)-6-($OSO_2CH_3$)-pyridine | | |
| 77 | 2-($ClCH_2CH_2CH_2SO$)-6-($OSO_2CH_3$)-pyridine | | |
| 78 | 2-($ClCH_2CH_2CH_2SO_2$)-6-($OSO_2CH_3$)-pyridine | | |

TABLE 1-continued $$R^1-S(O)_x+Ar+O-SO_2-R^2 \quad (I)$$

| Compound No. | formula | m.p. or b.p. (refractive index) | appearance |
|---|---|---|---|
| 79 | cyclopropyl-CH₂S-[pyridine]-OSO₂CH₃ | | |
| 80 | cyclopropyl-CH₂SO-[pyridine]-OSO₂CH₃ | | |
| 81 | cyclopropyl-CH₂SO₂-[pyridine]-OSO₂CH₃ | | |
| 82 | (CH₃)₃C-S-[pyridine]-OSO₂CH₃ | | |
| 83 | (CH₃)₃C-SO-[pyridine]-OSO₂CH₃ | | |
| 84 | (CH₃)₃C-SO₂-[pyridine]-OSO₂CH₃ | | |
| 85 | (CH₃)₃C-CH₂S-[pyridine]-OSO₂CH₃ | | |
| 86 | (CH₃)₃C-CH₂SO-[pyridine]-OSO₂CH₃ | | |
| 87 | (CH₃)₃C-CH₂SO₂-[pyridine]-OSO₂CH₃ | | |
| 88 | CH₃CH₂S-[pyridine]-OSO₂CH₃ | | |

TABLE 1-continued $$R^1-S(O)_x-(Ar)-O-SO_2-R^2 \quad (I)$$

| Compound No. | formula | m.p. or b.p. (refractive index) | appearance |
|---|---|---|---|
| 89 | CH₃CH₂SO—[pyridine]—OSO₂CH₃ | | |
| 90 | CH₃CH₂SO₂—[pyridine]—OSO₂CH₃ | | |
| 91 | (CH₃)₂CHCH₂S—[pyridine]—OSO₂CH₂Cl | | |
| 92 | (CH₃)₂CHCH₂SO—[pyridine]—OSO₂CH₂Cl | | |
| 93 | (CH₃)₂CHCH₂SO₂—[pyridine]—OSO₂CH₂Cl | | |
| 94 | CH₃CH₂CH₂S—[pyridine]—OSO₂CH₂CH₂CH₂Cl | ($n_D^{25}$ 1.5507) | colourless oil |
| 95 | CH₃CH₂CH₂SO—[pyridine]—OSO₂CH₂CH₂CH₂Cl | ($n_D^{25}$ 1.5481) | colourless oil |
| 96 | CH₃CH₂CH₂SO₂—[pyridine]—OSO₂CH₂CH₂CH₂Cl | m.p. 71–72° C. | colourless crystal |
| 97 | (CH₃)₂CHCH₂S—[pyridine]—OSO₂CH₂CH₃ | ($n_D^{25}$ 1.5361) | pale yellow oil |
| 98 | (CH₃)₂CHCH₂SO—[pyridine]—OSO₂CH₂CH₃ | | |

TABLE 1-continued
$$R^1-S(O)x-Ar-O-SO_2-R^2 \quad (I)$$
| Compound No. | formula | m.p. or b.p. (refractive index) | appearance |
|---|---|---|---|
| 99 | 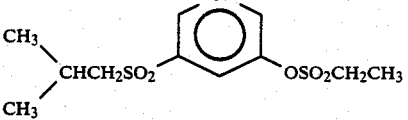 | | |
| 100 | 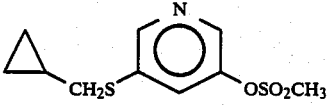 | | |
| 101 | 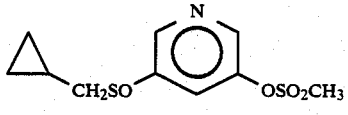 | | |
| 102 | 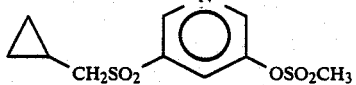 | | |
| 103 | 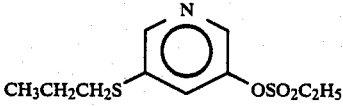 | | |
| 104 | 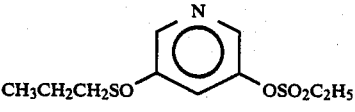 | | |
| 105 | 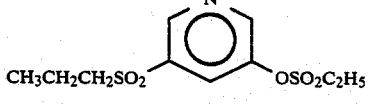 | | |
| 106 | 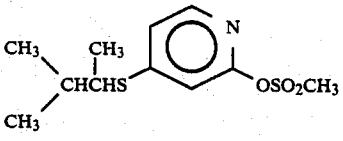 | | |
| 107 | 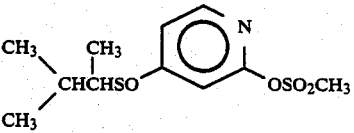 | | |
| 108 | 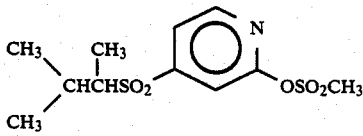 | | |
| 109 | 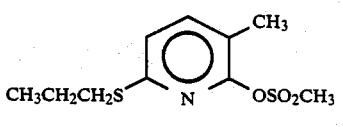 | | |

TABLE 1-continued $$R^1-S(O)_x+Ar+O-SO_2-R^2 \quad (I)$$

| Compound No. | formula | m.p. or b.p. (refractive index) | appearance |
|---|---|---|---|
| 110 | CH₃CH₂CH₂SO—[pyridine with 3-CH₃, 2-OSO₂CH₃, 6-position]—OSO₂CH₃ | | |
| 111 | CH₃CH₂CH₂SO₂—[pyridine with 3-CH₃, 2-OSO₂CH₃]—OSO₂CH₃ | | |
| 112 | ClCH₂CH₂CH₂S—[pyridine]—OSO₂CH₃ | | |
| 113 | ClCH₂CH₂CH₂SO—[pyridine]—OSO₂CH₃ | | |
| 114 | ClCH₂CH₂CH₂SO₂—[pyridine]—OSO₂CH₃ | | |
| 115 | (3,3,4,4-tetrafluorocyclobutyl)CH₂S—[pyridine]—OSO₂CH₃ | | |
| 116 | (3,3,4,4-tetrafluorocyclobutyl)CH₂SO—[pyridine]—OSO₂CH₃ | | |
| 117 | (3,3,4,4-tetrafluorocyclobutyl)CH₂SO₂—[pyridine]—OSO₂CH₃ | | |
| 118 | (CH₃)(CH₃CH₂)CHCH₂S—[pyridine]—OSO₂CH₃ | | |
| 119 | (CH₃)(CH₃CH₂)CHCH₂SO—[pyridine]—OSO₂CH₃ | | |
| 120 | (CH₃)(CH₃CH₂)CHCH₂SO₂—[pyridine]—OSO₂CH₃ | | |

TABLE 1-continued $$R^1-S(O)x\text{--}Ar\text{--}O-SO_2-R^2 \quad (I)$$

| Compound No. | formula | m.p. or b.p. (refractive index) | appearance |
|---|---|---|---|
| 121 | (CH₃)₂C(F)CH₂S—[pyridine-2,6-diyl]—OSO₂CH₃ | | |
| 122 | (CH₃)₂C(F)CH₂SO—[pyridine-2,6-diyl]—OSO₂CH₃ | | |
| 123 | (CH₃)₂C(F)CH₂SO₂—[pyridine-2,6-diyl]—OSO₂CH₃ | | |
| 124 | FCH₂CH₂CH₂S—[pyridine-2,4-diyl]—OSO₂CH₃ | | |
| 125 | FCH₂CH₂CH₂SO—[pyridine-2,4-diyl]—OSO₂CH₃ | | |
| 126 | FCH₂CH₂CH₂SO₂—[pyridine-2,4-diyl]—OSO₂CH₃ | | |
| 127 | FCH₂CH₂CH₂S—[pyridine-2,4-diyl]—OSO₂C₂H₅ | | |
| 128 | FCH₂CH₂CH₂S—[pyridine-3,5-diyl]—OSO₂CH₃ | | |
| 129 | FCH₂CH₂CH₂SO—[pyridine-3,5-diyl]—OSO₂CH₃ | | |
| 130 | FCH₂CH₂CH₂SO₂—[pyridine-3,5-diyl]—OSO₂CH₃ | | |
| 131 | FCH₂CH₂CH₂S—[pyridine-3,5-diyl]—OSO₂C₂H₅ | | |

TABLE 1-continued $$R^1-S(O)x-Ar-O-SO_2-R^2 \quad (I)$$

| Compound No. | formula | m.p. or b.p. (refractive index) | appearance |
|---|---|---|---|
| 132 | FCH₂CH₂CH₂S-(pyridine N-top, 3,5)-OSO₂CH₂Cl | | |
| 133 | CH₂CH₂OCH₂S-(pyridine N-bottom, 2,6)-OSO₂CH₃ | | |
| 134 | CH₃CH₂OCH₂SO-(pyridine N-bottom, 2,6)-OSO₂CH₃ | | |
| 135 | CH₃CH₂OCH₂SO₂-(pyridine N-bottom, 2,6)-OSO₂CH₃ | | |
| 136 | CH₃SCH₂CH₂S-(pyridine N-bottom, 2,6)-OSO₂CH₃ | ($n_D^{25}$ 1.6028) | colourless oil |
| 137 | CH₃SCH₂CH₂SO-(pyridine N-bottom, 2,6)-OSO₂CH₃ | | |
| 138 | CH₃SCH₂CH₂SO₂-(pyridine N-bottom, 2,6)-OSO₂CH₃ | | |
| 139 | (CH₃)₂CHCH₂SO-(3-methylpyridine, 2,6)-OSO₂CH₃ | | |
| 140 | (CH₃)₂CHCH₂SO₂-(3-methylpyridine, 2,6)-OSO₂CH₃ | ($n_D^{25}$ 1.5152) | colourless oil |
| 141 | cyclopropyl-CH₂S-(3-methylpyridine, 2,6)-OSO₂CH₃ | ($n_D^{25}$ 1.5554) | colourless oil |
| 142 | cyclopropyl-CH₂SO-(3-methylpyridine, 2,6)-OSO₂CH₃ | | |

TABLE 1-continued $$R^1-S(O)x+Ar+O-SO_2-R^2 \tag{I}$$

| Compound No. | formula | m.p. or b.p. (refractive index) | appearance |
|---|---|---|---|
| 143 | cyclopropyl-CH$_2$SO$_2$-[pyridine: 3-CH$_3$, 2-OSO$_2$CH$_3$] | mp 81–82° C. | colourless crystal |
| 144 | (CH$_3$)$_2$CHCH$_2$S-[pyridine: 3-CH$_3$, 2-OSO$_2$CH$_3$] | | |
| 145 | (CH$_3$)$_2$CHCH$_2$SO-[pyridine: 3-CH$_3$, 2-OSO$_2$CH$_3$] | | |
| 146 | (CH$_3$)$_2$CHCH$_2$SO$_2$-[pyridine: 3-CH$_3$, 2-OSO$_2$CH$_3$] | | |
| 147 | CH$_3$CH$_2$CH$_2$S-[pyridine: 3-CH$_3$, 2-OSO$_2$CH$_3$] | | |
| 148 | CH$_3$CH$_2$CH$_2$SO-[pyridine: 3-CH$_3$, 2-OSO$_2$CH$_3$] | | |
| 149 | CH$_3$CH$_2$CH$_2$SO$_2$-[pyridine: 3-CH$_3$, 2-OSO$_2$CH$_3$] | | |
| 150 | (CH$_3$)$_2$CHCH$_2$S-[pyridine: 3-CF$_3$, 2-OSO$_2$CH$_3$] | ($n_D^{25}$ 1.5402) | colourless oil |
| 151 | (CH$_3$)$_2$CHCH$_2$SO-[pyridine: 3-CF$_3$, 2-OSO$_2$CH$_3$] | | |
| 152 | (CH$_3$)$_2$CHCH$_2$SO$_2$-[pyridine: 3-CF$_3$, 2-OSO$_2$CH$_3$] | ($n_D^{25}$ 1.5144) | colourless oil |

TABLE 1-continued $$R^1-S(O)x-[Ar]-O-SO_2-R^2 \quad (I)$$

| Compound No. | formula | m.p. or b.p. (refractive index) | appearance |
|---|---|---|---|
| 153 | 3-CF$_3$, 2-OSO$_2$CH$_3$, 6-SCH$_2$CH$_2$CH$_3$ pyridine | | |
| 154 | 3-CF$_3$, 2-OSO$_2$CH$_3$, 6-S(O)CH$_2$CH$_2$CH$_3$ pyridine | | |
| 155 | 3-CF$_3$, 2-OSO$_2$CH$_3$, 6-SO$_2$CH$_2$CH$_2$CH$_3$ pyridine | | |
| 156 | 2-(cyclopentylthio)-6-(OSO$_2$CH$_2$CH$_3$) pyridine | mp 47–48° C. | colourless crystal |
| 157 | 2-(cyclopentylsulfonyl)-5-(OSO$_2$CH$_2$CH$_3$) pyridine | ($n_D^{25}$ 1.5322) | colourless oil |
| 158 | 2-(phenylthio)-6-(OSO$_2$CH$_3$) pyridine | mp 59.5–60.5° C. | colourless crystal |
| 159 | 2-(phenylsulfonyl)-6-(OSO$_2$CH$_3$) pyridine | mp 116–117° C. | colourless crystal |
| 160 | 4-CH$_3$, 2-((CH$_3$)$_2$CHCH$_2$S), 6-OSO$_2$CH$_2$CH$_3$ pyridine | ($n_D^{25}$ 1.5325) | pale yellow oil |
| 161 | 4-CH$_3$, 2-((CH$_3$)$_2$CHCH$_2$SO), 6-OSO$_2$CH$_2$CH$_3$ pyridine | mp 54–55° C. | colourless crystal |
| 162 | 4-CH$_3$, 2-((CH$_3$)$_2$CHCH$_2$SO$_2$), 6-OSO$_2$CH$_2$CH$_3$ pyridine | mp 63–65° C. | colourless crystal |

TABLE 1-continued $$R^1-S(O)x-(Ar)-O-SO_2-R^2 \quad (I)$$

| Compound No. | formula | m.p. or b.p. (refractive index) | appearance |
|---|---|---|---|
| 163 | 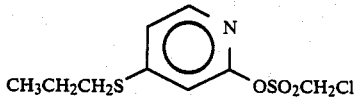 | ($n_D^{25}$ 1.5597) | colourless oil |

Synthesis Example 6: Preparation of 2-n-propylthio-4-methylsulfonyloxy-1,3-thiazole (No. 164)

8 g of 2-n-propylthio-1,3-thiazoline-4-one and 4.8 g of anhydrous sodium carbonate were suspended in acetonitrile, followed by stirring. 7.9 g of methanesulfonyl chloride was added dropwise to the suspension below 10° C. After the addition, the reaction was continued under stirring at room temperature for 2 hours. The reaction solution was poured into water and extracted by ether. The ether layer was washed with a saturated aqueous solution of common salt and dried over anhydrous sodium sulfate. The oil obtained by concentration was purified by silica-gel column chromatography to 9.1 g of the objective compound as a yellow oil (yield: 78.8%)

$n_D^{25}$ 1.5510

PMR(CDCl$_3$) δ: 1.05 (t, 3H), 1.78 (m, 2H), 3.12 (t, 2H), 3.32 (s, 3H), 6.76 (s, 1H) ppm.

Synthesis Example 7: Preparation of 2-isopropylthio-4-methylsulfonyloxy-1,3-thiazole (No. 171):

8 g of 2-isopropylthio-1,3-thiazoline-4-one was dissolved in 100 ml of methylene chloride and cooled below 10° C. Then, 7.8 g of methanesulfonyl chloride and 12.6 ml of triethylamine were added dropwise to the solution below 15° C. with attention to out-break of heat. After that, the reaction was continued with stirring at room temperature for 2 hours. Water was added to the reaction mixture and extracted by ether. The ether layer was washed with water and dried over anhydrous sodium sulfate. The oil obtained by concentration was purified by silica-gel column chromatography to obtain 9.1 g of the objective compound as a pale brown crystal (yield: 78.8%).

m.p 83° to 85° C.

PMR(CDCl$_3$) δ: 1.47 (d, 6H), 3.38 (s, 3H), 3.60~3.90 (m, 1H), 6.94 (s, 1H) ppm.

Synthesis Example 8: Preparation of 2-isopropylsulfonyl-4-methylsulfonyloxy-1,3-thiazole (No. 176):

2.5 g of 2-isopropylthio-4-methylsulfonyloxy-1,3-thiazole was dissolved in 10 ml of acetic acid. 2.9 ml of 35% aqueous hydrogen peroxide was added to the solution and the reaction was continued at 70° to 80° C. for 2 hours. The reaction mixture was poured into cold water and neutralized with 5% aqueous sodium hydroxide. The neutral solution was extracted by ethyl acetate and washed with saturated aqueous solution of common salt, followed by drying over anhydrous sodium sulfate to be concentrated to 2.5 g of a white crystal of the objective compound (yield: 88.7%).

m.p 56.5° to 58.5° C.

PMR(CDCl$_3$) δ: 1.48 (d, 6H), 3.48 (s, 3H), 3.48~3.80 (m, 1H), 7.66 (s, 1H) ppm.

Synthesis Example 9: Preparation of 2-sec-butylsulfinyl-4-methylsulfonyloxy-1,3-thiazole (No. 203):

4.0 g of 2-sec-butylthio-4-methylsulfonyloxy-1,3-thiazole was dissolved in 15 ml of acetic acid, and 2.2 ml of 35% aqueous hydrogen peroxide was added to the solution at room temperature, followed by reaction at 30° to 40° C. for 4 hours. The reaction mixture was poured into chilled water, neutralized by 5% aqueous solution of sodium hydroxide, and extracted with ethyl acetate. The extract was washed with a saturated aqueous solution of common salt, dried over anhydrous sodium sulfate and concentrated to obtain an oil, which was purified by silica-gel column chromatography to 2.1 g of the objective compound as a pale yellow oil (yield: 49.7%).

$n_D^{25}$ 1.5421

PMR(CDCl$_3$) δ: 1.04 to 1.56 (m, 6H), 1.56 to 2.44 (m, 2H), 3.08 to 3.48 (m, 1H), 3.66(s. 3H), 8.07 (s, 1H) ppm.

Synthesis Example 10: Preparation of 2-(3-fluoropropylthio)-4-methylsulfonyloxy-1,3-thiazole (No. 206):

6.2 g of 2-(3-fluoropropylthio)-1,3-thiazoline-4-one was dissolved in 80 ml of methylene chloride and cooled below 10° C. 5.5 g of methanesulfonyl chloride and 8.9 ml of triethylamine were added dropwise to the solution keeping the temperature below 15° C., followed by stirring at room temperature for 2 hours. After addition of water, the reaction mixture was extracted by methylene chloride, then organic layer is washed with water and dried over anhydrous sodium sulfate, followed by concentration to an oil, which is purified by silica-gel column chromatography to obtain 6.0 g of the objective compound as a pale brown oil (yield: 69.1%).

$n_D^{25}$ 1.5389

PMR(CDCl$_3$) δ: 1.90 to 2.20 (m, 2H), 3.16 to 3.40 (m, 2H), 3.28 (s, 3H), 4.24 (t, 1H), 4.70 (t, 1H), 6.74 (s, 1H) ppm.

Synthesis Example 11: Preparation of 2-isopropylthio-4-methylsulfonyloxy-5-chloro-1,3-thiazole (No. 230):

3.5 g of 2-isopropylthio-4-methylsulfonyloxy-1,3-thiazole (No. 171) was dissolved in 50 ml of methylene chloride. 2 g of sulfuryl chloride was added dropwise to the solution keeping the temperature below 0° C., followed by stirring at room temperature for 2 hours. Then, 20% aqueous solution of sodium carbonate was added to the reaction mixture to cease the reaction, and the methylene chloride layer was separated and washed with water, followed by drying over anhydrous sodium sulfate. The oil obtained by concentration was purified by silica-gel column chromatography to 2 g of the objective compound as a pale yellow oil (yield: 50.4%).
$n_D^{25}$ 1.5587
PMR(CDCl$_3$) δ: 1.45 (d, 6H), 3.46 (s, 3H), 3.60 to 4.00 (m, 1H) ppm.

Synthesis Example 12: Preparation of 2-isopropylthio-4-methylsulfonyloxy-5-bromo-1,3-thiazole (No. 233):

3.5 g of 2-isopropylthio-4-methylsulfonyloxy-1,3-thiazole was dissolved in 50 ml of ether, and 0.8 ml of bromine was added dropwise to the solution keeping the temperaure below 0° C. After the addition, the solution was stirred at room temperature for 2 hours, then 5% solution of sodium hydrogen sulfite was added thereto to separate ether layer, which was washed with water and dried over anhydrous sodium sulfate, followed by concentration to an oil. The oil was purified by silica-gel column chromatography to obtain 3.7 g of the objective compound as a yellow oil (yield: 80.7%).
$n_D^{25}$ 1.5763
PMR(CDCl$_3$) δ: 1.45 (d, 6H), 3.45 (s, 3H), 3.60 to 4.00 (m, 1H) ppm.

Other compounds of the present invention were synthesized according to the same procedure as the ones described in Synthesis Examples 6 to 12. Typical compounds among the obtained ones shown in Table 2.

TABLE 2

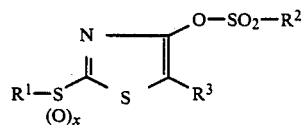

| Compound No. | R$^1$ | x | R$^2$ | R$^3$ | yield (%) | $n_D^{25}$ (mp °C.) | appearance |
|---|---|---|---|---|---|---|---|
| 164 | CH$_3$CH$_2$CH$_2$— | 0 | CH$_3$ | H | 78.8 | 1.5510 | yellow oil |
| 165 | CH$_3$CH$_2$CH$_2$— | 1 | CH$_3$ | H | 65.9 | 1.5462 | pale yellow oil |
| 166 | CH$_3$CH$_2$CH$_2$— | 2 | CH$_3$ | H | 88.7 | (83–85° C.) | colourless crystal |
| 167 | CH$_3$ | 0 | CH$_3$ | H | 74.6 | 1.5616 | brown oil |
| 168 | CH$_3$ | 2 | CH$_3$ | H | 73.5 | (97–98.5° C.) | colourless crystal |
| 169 | CH$_3$CH$_2$— | 0 | CH$_3$ | H | 66.5 | 1.5594 | pale brown oil |
| 170 | CH$_2$=CHCH$_2$— | 0 | CH$_3$ | H | 77.9 | 1.5669 | pale brown oil |
| 171 | (CH$_3$)$_2$CH— | 0 | CH$_3$ | H | 78.8 | (83–85° C.) | pale brown crystal |
| 172 | CH$_3$CH$_2$CH$_2$CH$_2$— | 0 | CH$_3$ | H | 86.7 | 1.5450 | pale brown oil |
| 173 | (CH$_3$)$_2$CHCH$_2$— | 0 | CH$_3$ | H | 79.7 | 1.5440 | pale brown oil |
| 174 | (CH$_3$)$_2$CHCH$_2$— | 2 | CH$_3$ | H | 96.8 | (58–60° C.) | colourless crystal |
| 175 | CH$_3$CH$_2$— | 2 | CH$_3$ | H | 79.4 | (57.5–59° C.) | coulourless crystal |
| 176 | (CH$_3$)$_2$CH— | 2 | CH$_3$ | H | 88.7 | (56.5–58.5° C.) | colourless crystal |
| 177 | CH$_2$=CHCH$_2$— | 2 | CH$_3$ | H | 11.8 | (77–79° C.) | colourless crystal |
| 178 | CH$_3$CH$_2$CH$_2$CH$_2$— | 2 | CH$_3$ | H | 85.7 | (75.5–76.5° C.) | colourless crystal |
| 179 | CH$_3$ | 1 | CH$_3$ | H | 56.1 | (71.5–73.5° C.) | colourless crystal |
| 180 | CH$_3$CH$_2$— | 1 | CH$_3$ | H | 49.8 | (63–65° C.) | colourless crystal |
| 181 | CH$_3$CH$_2$CH$_2$CH$_2$— | 1 | CH$_3$ | H | 77.8 | (48–49.5° C.) | colourless crystal |

TABLE 2-continued $$R^1-S(O)_x-C(=N-)-S-C(R^3)=C(O-SO_2-R^2)-$$

| Compound No. | R¹ | x | R² | R³ | yield (%) | $n_D^{25}$ (mp °C.) | appearance |
|---|---|---|---|---|---|---|---|
| 182 | (CH₃)₂CHCH₂— | 1 | CH₃ | H | 76.7 | (46–48° C.) | colourless crystal |
| 183 | (CH₃)₂CHCH₂CH₂— | 0 | CH₃ | H | 70.6 | 1.5392 | pale brown oil |
| 184 | CH₃CH₂CH₂CH₂CH₂CH₂— | 0 | CH₃ | H | 79.7 | 1.5330 | pale brown oil |
| 185 | ClCH₂CH₂CH₂— | 0 | CH₃ | H | 53.8 | 1.5662 | pale brown oil |
| 186 | ClCH₂CH₂CH₂— | 0 | —CH₂CH₃ | H | 43.3 | 1.5558 | pale brown oil |
| 187 | CH₃CH₂CH₂— | 0 | —CH₂CH₃ | H | 46.6 | 1.5452 | pale brown oil |
| 188 | CH≡CCH₂— | 0 | CH₃ | H | 77.3 | 1.5740 | pale brown oil |
| 189 | (CH₃)(CH₃CH₂)CH— | 0 | CH₃ | H | 73.4 | (41–43° C.) | pale yellow crystal |
| 190 | CH₃CH₂CH₂CH₂CH₂— | 0 | CH₃ | H | 73.5 | (44.5–45.5° C.) | pale yellow crystal |
| 191 | (CH₃)(CH₃CH₂CH₂)CH— | 0 | CH₃ | H | 76.3 | 1.5388 | pale brown oil |
| 192 | CH₂=CHCH₂— | 1 | CH₃ | H | 35.2 | (66–68° C.) | pale yellow crystal |
| 193 | (CH₃)₂CH— | 1 | CH₃ | H | 79.9 | (31.5–33° C.) | colourless crystal |
| 194 | ClCH₂CH₂CH₂— | 2 | CH₃ | H | 89.9 | (92–94° C.) | colourless crystal |
| 195 | ClCH₂CH₂CH₂— | 2 | —CH₂CH₃ | H | 72.6 | 1.5312 | colourless oil |
| 196 | CH₃CH₂CH₂— | 2 | —CH₂CH₃ | H | 96.2 | 1.5225 | colourless oil |
| 197 | (CH₃)₂CHCH₂CH₂— | 2 | CH₃ | H | 89.8 | (40.5–41.5° C.) | colourless crystal |
| 198 | CH₃CH₂CH₂CH₂CH₂CH₂— | 2 | CH₃ | H | 87.6 | (60–62° C.) | colourless crystal |
| 199 | (CH₃)(CH₃CH₂)CH— | 2 | CH₃ | H | 71.5 | 1.5230 | colourless oil |
| 200 | CH₃CH₂CH₂CH₂CH₂— | 2 | CH₃ | H | 89.7 | (73–74.5° C.) | colourless crystal |

TABLE 2-continued $$R^1-S(O)_x-C(=N)-S-C(R^3)=C(O-SO_2-R^2)$$

| Compound No. | R¹ | x | R² | R³ | yield (%) | $n_D^{25}$ (mp °C.) | appearance |
|---|---|---|---|---|---|---|---|
| 201 | CH₃(CH₃CH₂CH₂)CH— | 2 | CH₃ | H | 63.8 | 1.5185 | colourless oil |
| 202 | ClCH₂CH₂CH₂— | 1 | CH₃ | H | 66.9 | 1.5633 | colourless oil |
| 203 | CH₃(CH₃CH₂)CH— | 1 | CH₃ | H | 49.7 | 1.5421 | pale yellow oil |
| 204 | (CH₃)₂CHCH₂CH₂— | 1 | CH₃ | H | 84.1 | 1.5324 | pale yellow oil |
| 205 | (CH₃)₂CH— | 0 | —CH₂CH₃ | H | 49.9 | 1.5381 | pale brown oil |
| 206 | FCH₂CH₂CH₂— | 0 | CH₃ | H | 69.1 | 1.5389 | pale brown oil |
| 207 | FCH₂CH₂CH₂— | 2 | CH₃ | H | 82.6 | (88–89.5° C.) | colourless crystal |
| 208 | FCH₂CH₂CH₂— | 0 | —CH₂CH₃ | H | 41.3 | 1.5307 | pale yellow oil |
| 209 | C₆H₅CH₂— | 0 | CH₃ | H | 57.0 | 1.6007 | pale brown oil |
| 210 | C₆H₅CH₂— | 2 | CH₃ | H | 81.4 | (122–123° C.) | colourless crystal |
| 211 | (CH₃)₂CH— | 0 | CH₃ | CH₃ | 61.3 | (39.5–41° C.) | pale yellow crystal |
| 212 | (CH₃)₂CH— | 1 | CH₃ | CH₃ | 70.8 | 1.5329 | colourless oil |
| 213 | (CH₃)₂CH— | 2 | CH₃ | CH₃ | 77.4 | (70–71.5° C.) | colourless crystal |
| 214 | cyclopentyl— | 0 | CH₃ | H | 75.6 | (41–42.5° C.) | pale brown crystal |
| 215 | cyclopentyl— | 1 | CH₃ | H | 35.5 | 1.5572 | pale yellow oil |

TABLE 2-continued $$\underset{(O)_x}{R^1-S}\overset{N}{\underset{S}{\diagdown}}\hspace{-2pt}=\hspace{-2pt}\overset{O-SO_2-R^2}{\underset{R^3}{\diagup}}$$

| Compound No. | R¹ | x | R² | R³ | yield (%) | $n_D^{25}$ (mp °C.) | appearance |
|---|---|---|---|---|---|---|---|
| 216 | cyclopentyl-H | 2 | CH₃ | H | 84.0 | (104–105° C.) | colourless crystal |
| 217 | (CH₃)₂CHCH₂— | 0 | CH₃ | Cl | 56.1 | 1.5501 | pale brown oil |
| 218 | (CH₃)₂CHCH₂— | 1 | CH₃ | Cl | 63.3 | (85.5–87.5° C.) | colourless crystal |
| 219 | (CH₃)₂CHCH₂— | 2 | CH₃ | Cl | 90.4 | (68–69.5° C.) | colourless crystal |
| 220 | (CH₃)₂CHCH₂— | 0 | CH₃ | Br | 73.8 | 1.5709 | pale brown oil |
| 221 | (CH₃)₂CHCH₂— | 2 | CH₃ | Br | 87.0 | (74–75.5° C.) | colourless crystal |
| 222 | (CH₃)₂CH— | 0 | CH₃ | (*1) | 36.5 | 1.5284 | pale yellow oil |
| 223 | (CH₃)₂CH— | 2 | CH₃ | (*2) | 90.6 | 1.5129 | colourless oil |
| 224 | (CH₃)₂CH— | 0 | (*3) | H | 51.5 | 1.5302 | pale brown oil |
| 225 | (CH₃)₂CH— | 0 | (*4) | H | 70.4 | 1.5450 | pale brwon oil |
| 226 | (CH₃)₂CH— | 2 | (*5) | H | 79.4 | 1.5322 | colourless oil |
| 227 | cyclopentyl-H | 0 | (*6) | H | 52.4 | 1.5482 | pale brown oil |

TABLE 2-continued $$\underset{(O)_x}{R^1-S}\overset{N}{\underset{S}{\diagup}}\overset{O-SO_2-R^2}{\underset{R^3}{\diagdown}}$$

| Compound No. | R[1] | x | R[2] | R[3] | yield (%) | $n_D^{25}$ (mp °C.) | appearance |
|---|---|---|---|---|---|---|---|
| 228 | CH₃CH₂CH₂CH₂\CHCH₂—/CH₃CH₂ | 0 | CH₃ | H | 66.2 | 1.5290 | pale brown oil |
| 229 | CH₃CH₂CH₂CH₂\CHCH₂—/CH₃CH₂ | 2 | CH₃ | H | 94.5 | 1.5090 | colourless oil |
| 230 | CH₃\CH—/CH₃ | 0 | CH₃ | Cl | 50.4 | 1.5587 | pale yellow oil |
| 231 | ClCH₂CH₂CH₂— | 0 | CH₃ | Cl | 48.5 | 1.5780 | pale brown oil |
| 232 | (cyclopentyl-H) | 0 | CH₃ | Cl | 43.3 | (35–37° C.) | pale brown crystal |
| 233 | CH₃\CH—/CH₃ | 0 | CH₃ | Br | 80.7 | 1.5763 | yellow oil |
| 234 | ClCH₂CH₂CH₂— | 0 | CH₃ | Br | 67.3 | (44–46° C.) | pale brown crystal |
| 235 | (cyclopentyl-H) | 0 | CH₃ | Br | 55.8 | (44–46° C.) | brown crystal |
| 236 | (cyclopropyl-CH₂—) | 0 | CH₃ | H | 76.5 | 1.5655 | pale brown oil |
| 237 | (cyclopropyl-CH₂—) | 1 | CH₃ | H | 78.6 | (78.5–80.5° C.) | colourless crystal |
| 238 | (cyclopropyl-CH₂—) | 2 | CH₃ | H | 72.3 | 1.5417 | colourless oil |
| 239 | (cyclohexyl-H-ethyl) | 0 | CH₃ | H | 64.1 | (70–72° C.) | pale yellow crystal |
| 240 | (cyclohexyl-H-ethyl) | 1 | CH₃ | H | 76.7 | (59–61° C.) | colourless crystal |

TABLE 2-continued

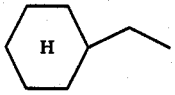

| Compound No. | R¹ | x | R² | R³ | yield (%) | $n_D^{25}$ (mp °C.) | appearance |
|---|---|---|---|---|---|---|---|
| 241 | (cyclohexyl-H with ethyl) | 2 | CH₃ | H | 78.5 | 1.5335 | colourless oil |

Note:
(*1) —CH₂CH₂CH₂CH₃
(*2) —CH₂CH₂CH₂CH₃,
(*3) —CH₂CH₂CH₂CH₃,
(*4) —CH₂CH₂CH₂Cl
(*5) —CH₂CH₂CH₂Cl,
(*6) —CH₂CH₂CH₃

FORMULATION EXAMPLE:

Formulation Example 1: Emulsifiable concentration 20 parts of a compound of the present invention was dissolved in 65 parts of a xylene/methylnaphthalene mixture. 15 parts of a mixture of the alkylphenol/ethylene oxide condensate and calcium alkylbenzenesulfonate in a ratio of 8:2 was mixed with the obtained solution to prepare an emulsifiable concentration. This emulsifiable concentration may be used as a spreading agent by diluting with water.

Formulation Example 2: Wettable powder 20 parts of a compound of the present invention was mixed with 35 parts of kaolin, 30 parts of clay and 7.5 parts of diatomaceous earth. 7.5 parts of a mixture of sodium laurate and sodium dinaphthylmethanesulfonate in a ratio of 1:1 was added to the obtained mixture. The resulting mixture was finely ground to prepare a powder. This powder may be used as a spreading agent by diluting with water.

Formulation Example 3: Dust 1 part of a compound of the present invention as mixed with 97 parts of a mixture of talc and calcium carbonate in a ratio 1:1. The resulting mixture was ground to prepare a homogeneously dispersed mixture. 2 parts of silicic acid anhydride was added to this mixture. The resulting mixture was mixed and ground to prepare a dust. This dust may be used as a spreading agent as such.

Formulation Example 4: Granule 2 parts of a compound of the present invention was mixed with 48 parts of finely powdered bentonite, 48 parts of talc and 2 parts of sodium ligninsulfonate, followed by the addition of water. The resulting mixture was kneaded until it became homogeneous. The mixture was granulated by passing it through an injection molding machine and adjusted to a granular size of 0.1 to 1 mm by passing the granule thus molded through a spherizer, a dryer and sieve. The obtained granule may be directly spreaded on the surface of paddy fields and uplands as such.

Formulation Example 5: Oil

A mixture of 0.1 part of a compound of the present invention and 0.5 part of piperonyl butoxide was dissolved in such amount of illuminating kerosene as to give the total volume of 100 parts to prepare an oil. This oil may be used as such.

Formulation Example 6: Aerosol 0.4 parts of a compound of the present invention, 20 parts of piperonyl butoxide, 6 parts of xylene and 7.6 parts of deodorized kerosine were mixed and dissolved. After filling the mixture into an aerosol container, a valve was fitted. 86 parts of Freon was introduced into the container through the valve under pressure to obtain an aerosol.

Formulation Example 7: Heating fibrous fumigant insecticidal composition 0.05 g of a compound of the present invention was dissolved in an appropriate amount of chloroform. The obtained solution was homogeneously adsorbed on the surface of an asbestos (2.5×1.5 mm, 0.3 mm in thickness) to prepare a fibrous fumigant insecticidal composition of hot plate heating type.

Formulation Example 8: Mosquito-repellant incense 0.5 g of a compound of the present invention was dissolved in 20 ml of methanol, followed by the addition of 99.5 g of an incense carrier comprising tabu powder, pyrethrum marc and wood powder in a ratio of 3:5:1. The obtained mixture was made homogeneous by stirring. After distilling off the methanol, 150 ml of water was added to the residue and the mixture was sufficiently kneaded, molded and dried to obtain a mosquito-repellant incense.

The effects of the present invention will be described by the following Test Examples.

The compounds used in the Test Examples as a control are the following comparative compounds (A), (B) and (C). These compounds were also tested according to the same method as the one for the test of compounds of the present invention.

(A) 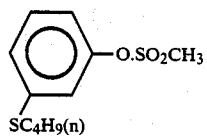 (Japanese Patent Publication No. 3898/1968)

(B) 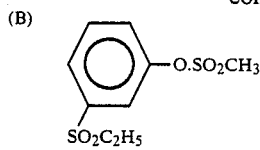 (Japanese Patent Laid-Open No. 98025/1973)

(C) 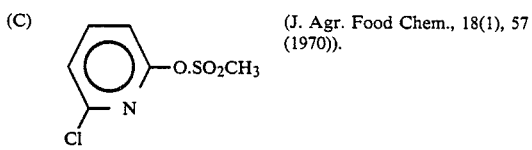 (J. Agr. Food Chem., 18(1), 57 (1970)).

TEST EXAMPLE:

Test Example 1: Effects on resistant and susceptible strains of *Nephotettix cincticepts*, respectively.

The compounds of the present invention and the comparative compounds were formulated according to the same procedure as the ones described in Formulation Examples 1 and 2 into 20% wettable powders when they were crystal, or into 20% emulsifiable concentration when they were oils, and were used for this test. Further, a 50% emulsifiable concentration of BPMC (2-sec-butylphenylmethylcarbamate) and a 40% emulsifiable concentration of Diazinon (diethyl-2-isopropyl-4-methyl-6-pyrimidinylphosphorothioate) were used as a control.

Method: 5 to 6 rice plants in the tri- to tetra-foliate stages were dipped in 200 ppm chemical solutions for 15 seconds. After air-drying, the plants were placed in a glass cylinder (4.5$\phi$, ×15 cm). Then, ten female adults of *Nephotettix cincticeps*, susceptible strain (collected in Ageo) and ten of the strain resistant to both organophosphorus and carbamates (collected in Nakagawara and in Izumi) were transferred in the cylinder. After covering with a wire mesh, the cylinder was left in a glass green-house. After 48 hours' treatment, the numbers of live and dead insects were counted to calculate the mortality. The results shown in Table 3 are averages of the two replications.

TABLE 3

| Compound for test | Mortality (%) | | |
|---|---|---|---|
| | Susceptible (collected in Ageo) | Resistant (collected in Nakagawara) | Resistant (collected in Izumi) |
| Compound No. | | | |
| 1 | 100 | 100 | 100 |
| 2 | 100 | 100 | 90 |
| 3 | 100 | 90 | 100 |
| 4 | 100 | 100 | 100 |
| 14 | 100 | 90 | 80 |
| 23 | 100 | 80 | 100 |
| 24 | 100 | 100 | 100 |
| 25 | 100 | 90 | 100 |
| 29 | 100 | 100 | 100 |
| 30 | 100 | 100 | 100 |
| 33 | 100 | 100 | 100 |
| 36 | 100 | 100 | 100 |
| 37 | 100 | 100 | 100 |
| 38 | 100 | 100 | 100 |
| 39 | 100 | 100 | 90 |
| 40 | 100 | 100 | 80 |
| 44 | 100 | 90 | 80 |
| 46 | 100 | 100 | 100 |
| 49 | 100 | 100 | 90 |
| 50 | 100 | 100 | 100 |
| 97 | 100 | 100 | 100 |
| 136 | 100 | 100 | 100 |
| 140 | 100 | 90 | 100 |
| 141 | 100 | 100 | 100 |
| 150 | 100 | 100 | 100 |
| 152 | 100 | 100 | 100 |
| 156 | 100 | 100 | 90 |
| 164 | 100 | 100 | 100 |
| 165 | 100 | 100 | 100 |
| 169 | 100 | 100 | 100 |
| 170 | 100 | 100 | 100 |
| 171 | 100 | 100 | 100 |
| 172 | 100 | 100 | 100 |
| 173 | 100 | 100 | 100 |
| 176 | 100 | 80 | 100 |
| 177 | 100 | 100 | 100 |
| 182 | 100 | 90 | 70 |
| 183 | 100 | 80 | 80 |
| 185 | 100 | 100 | 100 |
| 189 | 100 | 100 | 100 |
| 191 | 100 | 100 | 100 |
| 192 | 100 | 90 | 80 |
| 193 | 100 | 100 | 100 |
| 194 | 100 | 100 | 100 |
| 195 | 100 | 100 | 100 |
| 197 | 100 | 100 | 80 |
| 199 | 100 | 90 | 100 |
| 201 | 100 | 100 | 100 |
| 202 | 100 | 100 | 100 |
| 203 | 100 | 100 | 100 |
| 204 | 100 | 70 | 70 |
| 205 | 100 | 100 | 80 |
| 206 | 100 | 100 | 100 |
| 208 | 100 | 70 | 90 |
| 212 | 100 | 70 | 60 |
| 213 | 100 | 80 | 60 |
| 214 | 100 | 100 | 100 |
| 215 | 100 | 100 | 100 |
| 217 | 100 | 80 | 70 |
| 220 | 100 | 100 | 70 |
| 222 | 100 | 90 | 70 |
| 223 | 100 | 70 | 60 |
| 230 | 100 | 70 | 60 |
| 233 | 100 | 80 | 90 |
| 236 | 100 | 100 | 100 |
| 237 | 100 | 100 | 100 |
| 238 | 100 | 100 | 100 |
| Control | | | |
| A | 100 | 40 | 20 |
| B | 90 | 20 | 10 |
| C | 60 | 0 | 20 |
| Control BPMC | 100 | 20 | 0 |
| Diazinon | 100 | 0 | 30 |

Test Example 2: Effect on *Nilaparvata lugens*

The compounds of the present invention and the comparative compounds were formulated according to the same procedures as the ones described in Formulation Examples 1 and 2 into 20% wettable powder or into 20% emulsifiable concentration and tested.

Method: The same procedure described in Test Example 1 were repeated, except that 10 female adults of *Nilaparvata lugens* were used. 48 hours after treatment, the number of live and dead insects were counted to calculate the mortality. The results shown in Table 4 are averages of two replications. *Nilaparvata lugens*, ten susceptible strains (collected in Kaseda) and ten resistant strains (resistant to both organophosphorus and carbamates, collected in Izumi) was used in this test.

TABLE 4

| Compound for test | Mortality (%) | |
|---|---|---|
| | Susceptible (collected in Kaseda) | Resistant (collected in Izumi) |
| Compound No. | | |
| 1 | 100 | 100 |
| 2 | 100 | 100 |
| 3 | 100 | 100 |
| 4 | 100 | 100 |
| 7 | 100 | 70 |
| 21 | 100 | 80 |
| 24 | 100 | 100 |
| 29 | 100 | 90 |
| 30 | 100 | 100 |
| 33 | 100 | 100 |
| 36 | 100 | 100 |
| 37 | 100 | 100 |
| 41 | 100 | 80 |
| 44 | 100 | 80 |
| 45 | 100 | 90 |
| 49 | 100 | 100 |
| 50 | 100 | 100 |
| 140 | 100 | 100 |
| 141 | 100 | 80 |
| 150 | 100 | 100 |
| 152 | 100 | 100 |
| 156 | 100 | 100 |
| 160 | 100 | 90 |
| 163 | 100 | 100 |
| 164 | 100 | 100 |
| 165 | 100 | 90 |
| 166 | 100 | 80 |
| 168 | 100 | 100 |
| 169 | 100 | 100 |
| 170 | 100 | 70 |
| 171 | 100 | 100 |
| 172 | 100 | 100 |
| 173 | 100 | 100 |
| 174 | 100 | 100 |
| 175 | 100 | 100 |
| 176 | 100 | 100 |
| 177 | 100 | 100 |
| 178 | 100 | 60 |
| 179 | 100 | 60 |
| 180 | 100 | 70 |
| 181 | 100 | 100 |
| 182 | 100 | 100 |
| 183 | 100 | 60 |
| 184 | 100 | 70 |
| 185 | 100 | 90 |
| 187 | 100 | 100 |
| 189 | 100 | 100 |
| 190 | 100 | 100 |
| 192 | 100 | 80 |
| 193 | 100 | 100 |
| 194 | 100 | 80 |
| 195 | 100 | 70 |
| 196 | 100 | 70 |
| 197 | 100 | 60 |
| 199 | 100 | 90 |
| 201 | 100 | 100 |
| 202 | 100 | 100 |
| 203 | 100 | 100 |
| 204 | 100 | 80 |
| 205 | 100 | 90 |
| 206 | 100 | 100 |
| 207 | 100 | 70 |
| 208 | 100 | 80 |
| 211 | 100 | 80 |
| 214 | 100 | 100 |
| 215 | 100 | 100 |
| 216 | 100 | 70 |
| 217 | 100 | 100 |
| 218 | 100 | 80 |
| 219 | 100 | 60 |
| 220 | 100 | 100 |
| 221 | 100 | 70 |
| 222 | 100 | 60 |
| 223 | 100 | 60 |
| 227 | 100 | 70 |
| 228 | 100 | 80 |
| 230 | 100 | 60 |

TABLE 4-continued

| Compound for test | Mortality (%) | |
|---|---|---|
| | Susceptible (collected in Kaseda) | Resistant (collected in Izumi) |
| 232 | 100 | 70 |
| 233 | 100 | 70 |
| 235 | 100 | 70 |
| Control | | |
| A | 90 | 40 |
| B | 90 | 30 |
| C | 10 | 0 |
| Control BPMC | 100 | 10 |
| Diazinon | 100 | 20 |

Test Example 3: Effects on larvae of *Culex pipiens pallens*

The compounds of the present invention and the control were formulated into 0.1% acetone solution and tested.

Method: 199.8 ml of well water was placed in a plastic container having a diameter of 9 cm. Twenty larvae of *Culex pipiens pallens* (third to fourth instar), collected in Ageo, were transferred into the container. 0.2 ml of the above prepared solution was pipetted into the container to give a chemical solution of 1 ppm. After 24 hours, the numbers of live and dead insects were counted to calculate the mortality. The results shown in Table 5 are averages of the two replications.

TABLE 5

| Compound for test | Mortality (%) |
|---|---|
| Compound No. | |
| 1 | 100 |
| 2 | 100 |
| 3 | 100 |
| 4 | 100 |
| 5 | 100 |
| 6 | 100 |
| 14 | 100 |
| 15 | 100 |
| 16 | 80 |
| 17 | 100 |
| 18 | 100 |
| 19 | 90 |
| 20 | 100 |
| 21 | 100 |
| 22 | 100 |
| 23 | 100 |
| 24 | 100 |
| 25 | 100 |
| 26 | 80 |
| 27 | 80 |
| 28 | 80 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 42 | 80 |
| 43 | 80 |
| 44 | 100 |
| 45 | 100 |
| 46 | 100 |
| 47 | 100 |
| 48 | 100 |
| 49 | 100 |
| 50 | 100 |
| 51 | 100 |
| 94 | 100 |
| 95 | 100 |
| 96 | 80 |
| 97 | 100 |

TABLE 5-continued

| Compound for test | Mortality (%) |
|---|---|
| 136 | 100 |
| 140 | 100 |
| 150 | 100 |
| 152 | 100 |
| 156 | 100 |
| 157 | 100 |
| 158 | 100 |
| 159 | 100 |
| 160 | 100 |
| 161 | 100 |
| 162 | 100 |
| 163 | 100 |
| 164 | 100 |
| 165 | 100 |
| 166 | 100 |
| 169 | 100 |
| 170 | 100 |
| 171 | 100 |
| 172 | 100 |
| 173 | 100 |
| 174 | 100 |
| 176 | 100 |
| 177 | 80 |
| 178 | 100 |
| 180 | 80 |
| 181 | 100 |
| 182 | 100 |
| 183 | 100 |
| 184 | 100 |
| 185 | 100 |
| 186 | 100 |
| 187 | 100 |
| 188 | 70 |
| 189 | 100 |
| 190 | 100 |
| 191 | 100 |
| 192 | 100 |
| 193 | 100 |
| 194 | 100 |
| 195 | 90 |
| 196 | 100 |
| 197 | 100 |
| 198 | 100 |
| 199 | 100 |
| 200 | 100 |
| 201 | 100 |
| 202 | 100 |
| 203 | 100 |
| 204 | 100 |
| 205 | 100 |
| 206 | 100 |
| 207 | 100 |
| 208 | 100 |
| 209 | 100 |
| 210 | 100 |
| 211 | 100 |
| 214 | 100 |
| 215 | 100 |
| 216 | 100 |
| 217 | 100 |
| 218 | 100 |
| 219 | 100 |
| 220 | 100 |
| 221 | 100 |
| 222 | 70 |
| 223 | 70 |
| 224 | 90 |
| 225 | 70 |
| 226 | 80 |
| 227 | 100 |
| 228 | 100 |
| 229 | 100 |
| 230 | 100 |
| 231 | 100 |
| 232 | 100 |
| 233 | 100 |
| 234 | 100 |
| 235 | 100 |
| 236 | 100 |
| 237 | 100 |
| 238 | 100 |
| 239 | 100 |
| 240 | 100 |
| 241 | 100 |
| Control | |
| A | 70 |
| B | 30 |
| C | 0 |

Test Example 4: Effect on larvae of *Plutella xylostella*

The compounds of the present invention and the comparative compounds were formulated according to the same procedures as the ones described in Formulation Examples 1 and 2 into 20% wettable powders when they were crystals, or into 20% emulsifiable concentration when they were oils, and were used for this test. Further, 40% emulsifiable concentration of MEP (O,O-diethyl-O-4-nitro-m-tolyl phosphorothioate was used as a control.

Method: A cabbage leaf of a medium size cut from a cabbage grown to deca-foliate stage was dipped in a 500 ppm chemical solution for 15 seconds. After air-drying, the leaf was placed in a plastic container having a diameter of 9 cm. 15 larvae (third instar) of *Plutella xylostella* were transferred into the container. After covering with a lid having several pinholes, the container was left in a green house at 25° C. 48 hours after the treatment, the numbers of live and dead insects were counted to calculate the mortality. The results shown in Table 6 are averages of two replications.

TABLE 6

| Compound for test | Mortality (%) |
|---|---|
| Compound No. | |
| 3 | 100 |
| 4 | 100 |
| 20 | 100 |
| 21 | 100 |
| 23 | 100 |
| 34 | 100 |
| 37 | 100 |
| Control | |
| A | 10 |
| B | 0 |
| C | 0 |
| Control MEP | 70 |

Test Example 5: Effect on adults of *Tetranychus urticae*

The compounds of the present invention and the controls were formulated according to the same procedures as the ones described in Formulation Examples 1 and 2 into 20% wettable powders when they were crystals, or into 20% emulsifiable concentration when they were oils, and were used for this test.

Method: The primary leaf of a kidney bean which was cultivated in an unglazed pot (diameter: 9 cm) was trimmed to a size of approximately 3 cm×3 cm. 15 female adult mites susceptible to organophosphorus insecticide were transferred onto the leaf carefully using a small brush. The plants were left in a greenhouse adjusted at 25° C. After one day from the contact with the adults, dead and abnormal mites were taken out of the leaf. The mites on the leaf were dipped in a 400 ppm chemical solution for 10 seconds. After the treatement, the plant was left in the green-house. 48 hours after the treatment, the numbers of live and dead mites were counted under a stereomicroscope to calculate the mortality. The results are shown in Table 7.

TABLE 7

| Compound for test | Mortality (%) |
|---|---|
| Compound No. | |
| 3 | 100 |
| 7 | 100 |
| 8 | 100 |
| 9 | 100 |
| 18 | 100 |
| 24 | 100 |
| 171 | 100 |
| 175 | 100 |
| 176 | 100 |
| 177 | 100 |
| 185 | 100 |

Test Example 6: Effect on the clubroot of tomatoes due to *Meloidogine incognita*

400 g of soil polluted with *Meloidogine incognita* was packed in a plastic cup having a diameter of 10 cm. The compounds of the present invention, the comparative compounds and a control compound of DCIP [bis(2-chloromethylethyl)ether] were formulated according to the same procedure as the one described in Formulation Example 3 into 1% dusts. 40 mg of each dust was applied to the soil, followed by entire mixing. 15 seeds (variety: Ponte Rosa) were sown per cup.

40 days after the chemical treatment, the tomatoes were digged up and examined for damage due to chemicals and clubroot index. The results are shown in Table 7. The clubroot index was calculated by the following expression:

Clubroot index =

$$\frac{(A \times 4) + (B \times 3) + (C \times 2) + (D \times 1)}{(\text{number of examined seedlings}) \times 4} \times 100$$

A: Number of tomato seedlings having at least 31 clubroots.
B: Number of tomato seedlings having 21 to 30 clubroots.
C: Number of tomato seedlings having 11 to 20 clubroots.
D: Number of tomato seedlings having 1 to 10 clubroots.

The results are shown in Table 8.

TABLE 8

| Compound for test | Clubroot index | Phytotoxicity |
|---|---|---|
| Compound No. | | |
| 3 | 45 | no |
| 4 | 48 | no |
| 7 | 42 | no |
| 23 | 13 | no |
| 29 | 40 | no |
| 32 | 20 | no |
| 43 | 39 | no |
| Control (C) | 78 | no |
| Control DCIP | 83 | no |
| Untreated | 100 | — |

Test Example 7: Effect on larvae of *Anomala cuprea* in the soil 50 grams of chemical solution diluted with water, were fully mixed with 100 grams of dried soil containing dried leaf mold, and the treated soil was transferred to a plastic cup together with five 1st instar larvae of Cupreous chafer, *Anomala cuprea* and was kept in temperature controlled room (25° C.). After 2 days, the number of live and dead larvae was counted and mortalities were calculated. The results are shown in Table 9.

TABLE 9

| | Mortality (%) Concentration in soil | |
|---|---|---|
| Compound for test | 100 ppm | 10 ppm |
| Compound No. | | |
| 3 | 100 | 100 |
| 4 | 100 | 80 |
| 10 | 100 | 100 |
| 14 | 100 | 80 |
| 29 | 100 | 100 |
| 30 | 100 | 100 |
| 31 | 100 | 100 |
| 32 | 100 | 100 |
| 34 | 100 | 100 |
| 36 | 100 | 100 |
| 37 | 100 | 100 |
| 46 | 100 | 100 |
| 48 | 100 | 100 |
| 150 | 100 | 100 |
| 152 | 100 | 100 |
| 164 | 100 | 100 |
| 165 | 100 | 100 |
| 169 | 100 | 100 |
| 170 | 100 | 100 |
| 171 | 100 | 80 |
| 173 | 100 | 100 |
| 176 | 100 | 80 |
| 182 | 100 | 100 |
| 185 | 100 | 80 |
| 189 | 100 | 100 |
| 190 | 100 | 60 |
| 193 | 100 | 100 |
| 206 | 100 | 100 |
| Untreated | 0 | 0 |

What we claim is:
1. A compound of the formula:

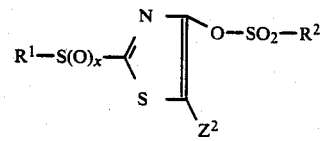

wherein
$Z^2$ is hydrogen, halogen, $C_1$-$C_4$-alkyl unsubstituted or substituted with halogen,
$R^1$ is $C_1$-$C_8$-alkyl; $C_1$-$C_7$-alkyl which is substituted by 1-3 of F, Cl or Br, $C_1$-$C_4$-alkoxy or $C_1$-$C_4$-alkylthio; $C_3$-$C_7$-cycloalkyl unsubstituted or substituted with 1-4 of F, Cl or methyl; $C_3$-$C_6$-cycloalkylmethyl unsubstituted or substituted with 1-4 of F, Cl, Br or methyl; allyl; propargyl; phenyl or benzyl; $R^2$ is $C_1$-$C_4$-alkyl unsubstituted or substituted with 1-3 of F or Cl,
x is integer of 0, 1 or 2.

2. A compound of the formula (I) according to claim 1, wherein $Z^2$ is hydrogen, halogen, $C_1$-$C_4$-alkyl unsubstituted or substituted with halogen, $R^1$ is $C_2$-$C_5$-alkyl unsubstituted or substituted with F or Cl; $C_3$-$C_6$-cycloalkyl; $C_3$-$C_6$-cycloalkylmethyl or allyl; $R^2$ is $CH_3$, $CH_2Cl$ or $C_2H_5$ and x is 0, 1 or 2.

3. A compound of Formula (I) according to claim 2 wherein $Z^2$ is hydrogen or bromine, $R^1$ is $C_2H_5$, n—$C_3H_7$, iso—$C_3H_7$, n—$C_4H_9$, sec—$C_4H_9$, iso—$C_4H_9$, —CH₂CH₂CH₂Cl, —Ch₂CH₂CH₂F, —CH₂CH=CH₂, cyclopentyl or cyclopropylmethyl, R² is CH₃ or Ch₂Cl, x is 0, 1 or 2.

4. A compound of the Formula (I) according to claim 3 which is selected from the group consisting of one of the following formula:

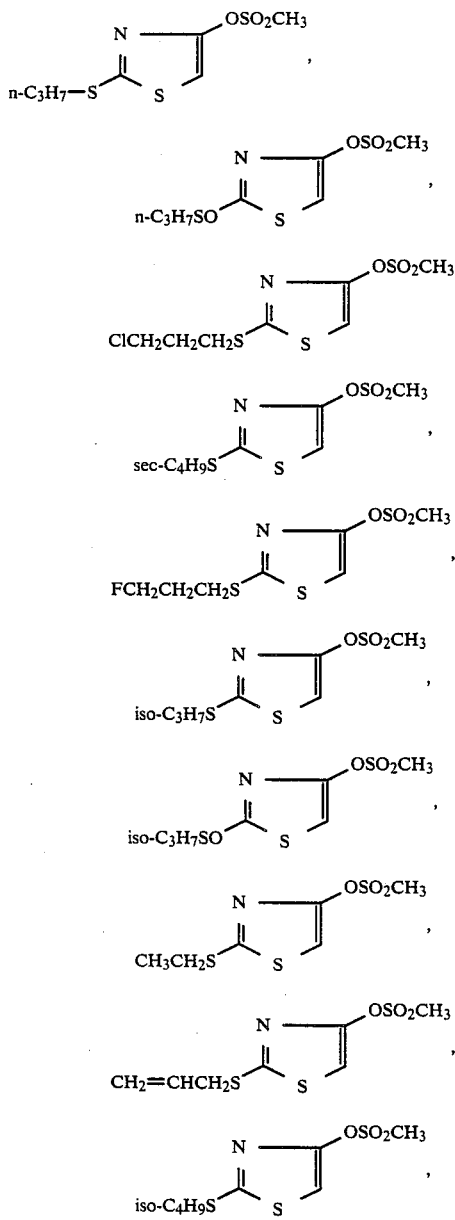

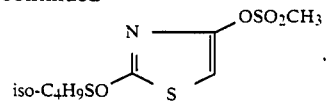

5. An insecticidal, acaricidal or nematicidal composition which comprises an effective amount of a compound of the formula:

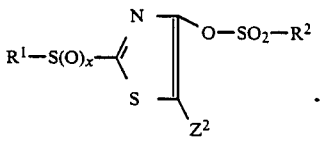

wherein
$Z^2$ is hydrogen, halogen, $C_1$-$C_4$-alkyl unsubstituted or substituted with halogen,
$R^1$ is $C_1$-$C_8$-alkyl; $C_1$-$C_7$-alkyl which is substituted by 1-3 of F, Cl or Br, $C_1$-$C_4$-alkoxy or $C_1$-$C_4$-alkylthio; $C_3$-$C_7$-cycloalkyl unsubstituted or substituted with 1-4 of F, Cl or methyl; $C_3$-$C_6$-cycloalkylmethyl unsubstituted or substituted with 1-4 of F, Cl, Br or methyl; alkyl; propargyl; phenyl or benzyl; $R^2$ is $C_1$-$C_4$-alkyl unsubstituted or substituted with 1-3 of F or Cl,
x is integer of 0, 1 or 2, as an effective component in admixture with an inert carrier.

6. A method for killing insect pests, acarids or nematodes, which comprises applying to insect pests, acarids or nematodes an effective amount of a compound of the formula:

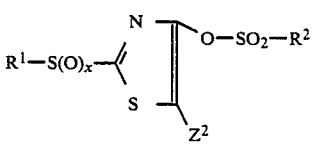

wherein
$Z^2$ is hydrogen, halogen, $C_1$-$C_4$-alkyl unsubstituted or substituted with halogen,
$R^1$ is $C_1$-$C_8$-alkyl; $C_1$-$C_7$-alkyl which is substituted by 1-3 of F, Cl or Br, $C_1$-$C_4$-alkoxy or $C_1$-$C_4$-alkylthio; $C_3$-$C_7$-cycloalkyl unsubstituted or substituted with 1-4 of F, Cl or methyl; $C_3$-$C_6$-cycloalkylmethyl unsubstituted or substituted with 1-4 of F, Cl, Br or methyl; allyl; propargyl; phenyl or benzyl; $R^2$ is $C_1$-$C_4$-alkyl unsubstituted or substituted with 1-3 of F or Cl,
x is integer of 0, 1 or 2, to said insect pests, acarids or nematodes.

* * * * *